US011008582B2

(12) United States Patent
De Bont et al.

(10) Patent No.: US 11,008,582 B2
(45) Date of Patent: May 18, 2021

(54) PLANTS WITH INCREASED YIELD AND METHOD FOR PRODUCING SAID PLANTS

(71) Applicants: CENTRE NATIONAL DE LA RECHERCHE SCIENTIFIQUE (CNRS), Paris (FR); UNIVERSITE PARIS-SUD, Orsay (FR)

(72) Inventors: Linda De Bont, Les Ulis (FR); Bertrand Gakiere, Gif S/Yvette (FR)

(73) Assignees: CENTRE NATIONAL DE LA RECHERCHE SCIENTIFIQUE (CNRS), Paris (FR); UNIVERSITE PARIS-SUB, Orsay (FR)

( * ) Notice: Subject to any disclaimer, the term of this patent is extended or adjusted under 35 U.S.C. 154(b) by 163 days.

(21) Appl. No.: 15/120,829

(22) PCT Filed: Feb. 24, 2015

(86) PCT No.: PCT/EP2015/053850
§ 371 (c)(1),
(2) Date: Aug. 23, 2016

(87) PCT Pub. No.: WO2015/124799
PCT Pub. Date: Aug. 27, 2015

(65) Prior Publication Data
US 2016/0362702 A1  Dec. 15, 2016

(30) Foreign Application Priority Data
Feb. 24, 2014  (FR) ........................................ 1451445

(51) Int. Cl.
| | | |
|---|---|---|
| *C12N 15/82* | (2006.01) | |
| *C07K 14/415* | (2006.01) | |
| *A01H 1/02* | (2006.01) | |
| *A01H 1/04* | (2006.01) | |
| *C12N 9/06* | (2006.01) | |
| *C12Q 1/6895* | (2018.01) | |

(52) U.S. Cl.
CPC ........... *C12N 15/8261* (2013.01); *A01H 1/02* (2013.01); *A01H 1/04* (2013.01); *C07K 14/415* (2013.01); *C12N 9/0022* (2013.01); *C12N 15/8267* (2013.01); *C12N 15/8271* (2013.01); *C12N 15/8273* (2013.01); *C12N 15/8279* (2013.01); *C12N 15/8281* (2013.01); *C12N 15/8286* (2013.01); *C12Q 1/6895* (2013.01); *C12Y 104/03016* (2013.01); *C12Q 2600/13* (2013.01); *C12Q 2600/158* (2013.01); *Y02A 40/146* (2018.01)

(58) Field of Classification Search
None
See application file for complete search history.

(56) References Cited

U.S. PATENT DOCUMENTS

| | | | | |
|---|---|---|---|---|
| 6,271,031 B1 * | 8/2001 | Falco | ................... | C12N 9/0022 435/189 |
| 2007/0016976 A1 | 1/2007 | Katagiri et al. | | |
| 2011/0283418 A1 * | 11/2011 | McKersie | .......... | C12N 15/8261 800/288 |
| 2013/0310585 A1 | 11/2013 | Wang et al. | | |

FOREIGN PATENT DOCUMENTS

| | | |
|---|---|---|
| EP | 2 573 179 A1 | 3/2013 |
| WO | WO 99/04012 A1 | 1/1999 |
| WO | WO 2010/086220 A1 | 8/2010 |

OTHER PUBLICATIONS

Zhong et al. (Euphytica 118: 137-144, 2001). (Year: 2001).*
Bulbul, "A Fungal Rust Effector Targets the Plant Cell Nucleus and Modulates Transcription." (2017): 192. (Year: 2017).*
GenBank Accession BT001009 dated Oct. 18, 2002. (Year: 2002).*
Schmidt et al. (Crop science 44.3 (2004): 963-967). (Year: 2004).*
Tedeschi et al. (Biochemistry 36.51 (1997):16221-16230). (Year: 1997).*
Bechtold et al., "In-planta Agrobacterium-mediated Gene-transfer by Infiltration of Adult *Arabidopsis-thaliana* Plants," Comptes Rendus De L Academie Des Sciences Serie III—Sciences De La Vie-Life Sciences, vol. 316, Issue 10, Oct. 1993, 2 pages, Abstract only.
Benfey et al., "The CaMV 35S Enhancer Contains at least Two Domains which Can Confer Different Developmental and Tissue-specific Expression patterns," The EMBO Journal, vol. 8, No. 8, 1989, pp. 2195-2202.
Christou et al., "Production of Transgenic Rice (*Oryza sativa* L.) Plants from Agronomically Important Indica and Japonica Varieties via Electric Discharge Particle Acceleration of Exogenous DNA into Immature Zygotic Embryos," Nature Biotechnology, vol. 9, 1991, 2 pages, Abstract only.
Chupeau et al., "Transgenic Plants of Lettuce (*Lactuca sativa*) Obtained Through Electroporation of Protoplasts," Nature Biotechnology, vol. 7, 1989, 2 pages, Abstract only.
Eckstein, "Oligonucleotides and Analogues: A Practical Approach," Book Review in Brief, Biochemical Education, vol. 20, No. 2, 1992 (IRL Press at Oxford University Press 1991), pp. 96.
Finer et al., "Development of the Particle Inflow Gun for DNA Delivery to Plant Cells," Plant Cell Reports, vol. 11, 1992, pp. 323-328.
Fromm et al., "Inheritance and Expression of Chimeric Genes in the Progeny of Transgenic Maize Plants," Nature Biotechnology, vol. 8, 1990, 2 pages, Abstract only.

(Continued)

*Primary Examiner* — Charles Logsdon
(74) *Attorney, Agent, or Firm* — Birch, Stewart, Kolasch & Birch, LLP

(57) ABSTRACT

The invention relates to a method for increasing the yield and biomass of a plant, by means of an increase in the expression of the L-aspartate oxidase in the plant. The method according to the invention allows an increase in the photosynthetic capacities of the plants as a result of an increase in the quantities of NAD and the derivatives thereof in said plants. The invention relates to the plants produced by such a method.

16 Claims, 12 Drawing Sheets

Specification includes a Sequence Listing.

(56) References Cited

OTHER PUBLICATIONS

Hiei et al., "Efficient Transformation of Rice (*Oryza sativa* L.) Mediated by Agrobacterium and Sequence Analysis of the Boundaries of the T-DNA," The Plant Journal, vol. 6, No. 2, 1994, pp. 271-282.

Hiei et al., "Transformation of Rice Mediated by Agrobacterium tumefaciens," Plant Molecular Biology, Vo. 35, 1997, pp. 205-218.

Ishida et al., "High Efficiency Transformation of Maize (*Zea mays* L.) Mediated by Agrobacterium tumefaciens," Nature Biotechnology, vol. 14, 1996, 2 pages, Abstract only.

Kebeish et al., "Chloroplastic Photorespiratory Bypass Increases Photosynthesis and Biomass Production in *Arabidopsis thaliana*," Nature Biotechnology, vol. 25, No. 5, May 2007 (published online Apr. 15, 2007), pp. 593-599 (Total 8 pages).

Lin et al., "Synthesizing and Salvaging NAD+: Lessons Learned from Chlamydomonas reinhardtii," PLoS Genetics, vol. 6, Issue No. 9, Sep. 2010, e1001105, pp. 1-15, XP55085362A.

Macho et al., "Aspartate Oxidase Plays an Important Role in *Arabidopsis stomatal* Immunity," Plant Physiology, vol. 159, Aug. 2012, pp. 1845-1856 (Total 15 pages), XP55150776A.

Maier et al., "Transgenic Introduction of a Glycolate Oxidative Cycle into *A. thaliana* Chloroplasts Leads to Growth Improvement," Frontiers in Plant Science, vol. 3, Article 38, Feb. 28, 2012, pp. 1-12.

Mcelroy et al., "Construction of Expression Vectors Based on the Rice Actin 1 (Act1) 5' Region for Use in Monocot Transformation," Mol Gen Genet, vol. 231, 1991, pp. 150-160.

Neuhaus et al., "Transgenic Rapeseed Plants Obtained by the Microinjection of DNA into Microspore-derived Embryoids," Theor Appl Genet, vol. 75, 1987, pp. 30-36.

Noctor et al., "NAD(P) Synthesis and Pyridine Nucleotide Cycling in Plants and their Potential Importance in Stress Conditions," Journal of Experimental Botany, vol. 57, No. 8, 2006 (Advance Access publication May 12, 2006), pp. 1603-1620 (Total 19 pages).

Schocher et al., "Co-Transformation of Unlinked Foreign Genes into Plants by Direct Gene Transfer," Nature Biotechnology, vol. 4, 1986, 2 pages, Abstract only.

Written Opinion of the International Searching Authority and International Search Report (forms PCT/ISA/237 and PCT/ISA/210), dated May 20, 2015, for International Application No. PCT/EP2015/053850.

* cited by examiner

SEQUENCE LISTING

```
<160> NUMBER OF SEQ ID NOS: 20

<210> SEQ ID NO 1
<211> LENGTH: 3912
<212> TYPE: DNA
<213> ORGANISM: Arabidopsis thaliana

<400> SEQUENCE: 1
atggcggctc atgtttctac tggaaacatt cataatttct atcttgcggg gcaggtttac      60
aggggacaag cttttcatg gagttctgct tctactttca tggcaaatcc attcaaagag     120
ccctcttggt caagtggggt atttaaggct ctaaaagctg agagatgtgg ttgttactct     180
cgtggtattt cccccatcag tgagacctca aaacctatca gggctgtttc ggtatcttct     240
tcaacaaagt attatgattt cactgtgatt ggtagtggag tagcgggtct gcgttatgct     300
ttagaagttg caaagcaagg aacagtcgca gtgattacca aagatgagcc tcatgagagt     360
aacacaaact atgctcaagg tggtgttagt gctgtgttat gcccttttgga ttctgttgaa     420 agtcatatgc gggacactat ggtcgctggt gctcatcttt gtgatgaaga aaccgtaaga     480
gttgtgtgta ctgaagggcc tgaaaggatt cgtgaactga ttgcaatggg agcatcattt     540
gatcacggcg aggatggaaa tttgcatttg gccagagagg gtggtcactc gcattgtagg     600
atcgttcacg ctgctgatat gacaggaaga gagattgaga gagctttact tgaagctgta     660
cttaatgatc ccaacatatc tgtcttcaaa caccattttg caatcgatct gctcacttct     720
caggatggct tgaacacagt ttgtcatggt gtggacactt tgaatatcaa aactaatgag     780
gtagtacgct ttatatcgaa ggtgacattg cttgcttcag gtggagctgg gcatatctat     840
ccatcaacca caaatcctct ggtggctact ggagatggga tggcgatggc tcatcgagct     900
caagctgtga tctcaaatat ggaatttgtg cagtttcatc ctactgccct agccgacgaa     960
ggtcttccca tcaaactaca aactgctagg gaaaacgcgt tcctcatcac cgaggcggtg    1020
agaggtgatg gtggcatcct ctataatcta ggaatggagc gattcatgcc tgtttacgat    1080
gaacgagctg agcttgctcc aagagacgtg gttgcaagaa gtattgatga ccagcttaag    1140
```

```
aaacgaaacg aaaagtatgt gttacttgac ataagccata agccaagaga aagattctt    1200 gcccatttcc cgaacatagc ttctgaatgt cttaaacacg gtctggatat cacccgtcag   1260
cctattccgg ttgtccctgc agcccattac atgtgtggag gagttcgtgc tggtttacaa   1320
ggcgaaacca atgtccttgg attgtttgta gcaggtgaag tagcatgtac aggcctccac   1380
ggggcaaatc gtcttgctag taactcgctt ttagaagctc tggttttcgc gagacgggct   1440
gttcagcctt cgactgagct catgaaacgc acaagacttg atgtatgcgc atcagagaaa   1500
tggacaaggc ctgttgttgc gacagctaga ttgctaggag atgaagtaat agcaaagatt   1560
atagctttga ctaaagaagt gagaagagag cttcaggagg taatgtggaa gtatgttggt   1620
attgtcagat cgacaattcg gctcaccact gctgagagga aaatcgcaga gctagaagca   1680
aaatgggaaa cattttgtt tgaacatgga tgggaacaaa cagtggtagc tcttgaagct    1740
tgtgagatga gaaacttgtt ctgttgcgct aagcttgtgg tgagcagcgc gttagctaga   1800
catgaaagca gaggtcttca ttacatgaca gactttcctt ttgtggaaga aagcaagcgg   1860
attccgacga ttattctacc gtcttctcct acaacagcta gttggagctc aaggcggtta   1920
cagaatataa gtagcagctc acttattgat tgctaaatgg cggctcatgt ttctactgga   1980
aacattcata atttctatct tgcggggcag gtttacaggg gacaagcttt tcatggagt    2040 tctgcttcta ctttcatggc aaatccattc aaagagccct cttggtcaag tggggtattt   2100
aaggctctaa aagctgagag atgtggttgt tactctcgtg gtatttcccc catcagtgag   2160
acctcaaaac ctatcagggc tgtttcggta tcttcttcaa caaagtatta tgatttcact   2220
gtgattggta gtggagtagc gggtctgcgt tatgctttag aagttgcaaa gcaaggaaca   2280
gtcgcagtga ttaccaaaga tgagcctcat gagagtaaca caaactatgc tcaaggtggt   2340
gttagtgctg tgttatgccc tttggattct gttgaaagtc atatgcggga cactatggtc   2400
gctggtgctc atctttgtga tgaagaaacc gtaagagttg tgtgtactga agggcctgaa   2460
aggattcgtg aactgattgc aatgggagca tcatttgatc acggcgagga tggaaatttg   2520
catttggcca gagagggtgg tcactcgcat tgtaggatcg ttcacgctgc tgatatgaca   2580
ggaagagaga ttgagagagc tttacttgaa gctgtactta atgatcccaa catatctgtc   2640
ttcaaacacc attttgcaat cgatctgctc acttctcagg atggcttgaa cacagtttgt   2700
catggtgtgg acactttgaa tatcaaaact aatgaggtag tacgctttat atcgaaggtg   2760
acattgcttg cttcaggtgg agctgggcat atctatccat caaccacaaa tcctctggtg   2820
gctactggag atgggatggc gatggctcat cgagctcaag ctgtgatctc aaatatggaa   2880
tttgtgcagt tcatcctac tgccctagcc gacgaaggtc ttcccatcaa actacaaact    2940
gctagggaaa acgcgttcct catcaccgag gcggtgagag tgatggtgg catcctctat    3000 aatctaggaa tggagcgatt catgcctgtt tacgatgaac gagctgagct tgctccaaga   3060
gacgtggttg caagaagtat tgatgaccag cttaagaaac gaaacgaaaa gtatgtgtta   3120
cttgacataa gccataagcc aagagaaaag attcttgccc atttcccgaa catagcttct   3180
gaatgtctta aacacggtct ggatatcacc cgtcagccta ttccggttgt ccctgcagcc   3240
cattacatgt gtgaggagt tcgtgctggt ttacaaggcg aaaccaatgt ccttggattg    3300
tttgtagcag gtgaagtagc atgtacaggc ctccacgggg caaatcgtct tgctagtaac   3360
tcgcttttag aagctctggt tttcgcgaga cgggctgttc agccttcgac tgagctcatg   3420
aaacgcacaa gacttgatgt atgcgcatca gagaaatgga caaggcctgt tgttgcgaca   3480
```

```
gctagattgc taggagatga agtaatagca aagattatag ctttgactaa agaagtgaga  3540
agagagcttc aggaggtaat gtggaagtat gttggtattg tcagatcgac aattcggctc  3600
accactgctg agaggaaaat cgcagagcta gaagcaaaat gggaaacatt tttgtttgaa  3660
catggatggg aacaaacagt ggtagctctt gaagcttgtg agatgagaaa cttgttctgt  3720
tgcgctaagc ttgtggtgag cagcgcgtta gctagacatg aaagcagagg tcttcattac  3780
atgacagact ttccttttgt ggaagaaagc aagcggattc cgacgattat tctaccgtct  3840
tctcctacaa cagctagttg gagctcaagg cggttacaga atataagtag cagctcactt  3900
attgattgct aa                                                     3912
```

<210> SEQ ID NO 2
<211> LENGTH: 651
<212> TYPE: PRT
<213> ORGANISM: Arabidopsis thaliana

<400> SEQUENCE: 2

```
Met Ala Ala His Val Ser Thr Gly Asn Ile His Asn Phe Tyr Leu Ala
1               5                   10                  15

Gly Gln Val Tyr Arg Gly Gln Ala Phe Ser Trp Ser Ser Ala Ser Thr
            20                  25                  30

Phe Met Ala Asn Pro Phe Lys Glu Pro Ser Trp Ser Ser Gly Val Phe
        35                  40                  45

Lys Ala Leu Lys Ala Glu Arg Cys Gly Cys Tyr Ser Arg Gly Ile Ser
    50                  55                  60

Pro Ile Ser Glu Thr Ser Lys Pro Ile Arg Ala Val Ser Val Ser Ser
65                  70                  75                  80

Ser Thr Lys Tyr Tyr Asp Phe Thr Val Ile Gly Ser Gly Val Ala Gly
                85                  90                  95

Leu Arg Tyr Ala Leu Glu Val Ala Lys Gln Gly Thr Val Ala Val Ile
            100                 105                 110

Thr Lys Asp Glu Pro His Glu Ser Asn Thr Asn Tyr Ala Gln Gly Gly
        115                 120                 125

Val Ser Ala Val Leu Cys Pro Leu Asp Ser Val Glu Ser His Met Arg
    130                 135                 140

Asp Thr Met Val Ala Gly Ala His Leu Cys Asp Glu Glu Thr Val Arg
145                 150                 155                 160

Val Val Cys Thr Glu Gly Pro Glu Arg Ile Arg Glu Leu Ile Ala Met
                165                 170                 175

Gly Ala Ser Phe Asp His Gly Glu Asp Gly Asn Leu His Leu Ala Arg
            180                 185                 190

Glu Gly Gly His Ser His Cys Arg Ile Val His Ala Ala Asp Met Thr
        195                 200                 205

Gly Arg Glu Ile Glu Arg Ala Leu Leu Glu Ala Val Leu Asn Asp Pro
    210                 215                 220

Asn Ile Ser Val Phe Lys His His Phe Ala Ile Asp Leu Leu Thr Ser
225                 230                 235                 240

Gln Asp Gly Leu Asn Thr Val Cys His Gly Val Asp Thr Leu Asn Ile
                245                 250                 255

Lys Thr Asn Glu Val Val Arg Phe Ile Ser Lys Val Thr Leu Leu Ala
            260                 265                 270

Ser Gly Gly Ala Gly His Ile Tyr Pro Ser Thr Thr Asn Pro Leu Val
        275                 280                 285

Ala Thr Gly Asp Gly Met Ala Met Ala His Arg Ala Gln Ala Val Ile
```

```
                 290                 295                 300
Ser Asn Met Glu Phe Val Gln Phe His Pro Thr Ala Leu Ala Asp Glu
305                 310                 315                 320

Gly Leu Pro Ile Lys Leu Gln Thr Ala Arg Glu Asn Ala Phe Leu Ile
                325                 330                 335

Thr Glu Ala Val Arg Gly Asp Gly Ile Leu Tyr Asn Leu Gly Met
                340                 345                 350

Glu Arg Phe Met Pro Val Tyr Asp Glu Arg Ala Glu Leu Ala Pro Arg
                355                 360                 365

Asp Val Val Ala Arg Ser Ile Asp Asp Gln Leu Lys Lys Arg Asn Glu
370                 375                 380

Lys Tyr Val Leu Leu Asp Ile Ser His Lys Pro Arg Glu Lys Ile Leu
385                 390                 395                 400

Ala His Phe Pro Asn Ile Ala Ser Glu Cys Leu Lys His Gly Leu Asp
                405                 410                 415

Ile Thr Arg Gln Pro Ile Pro Val Val Pro Ala Ala His Tyr Met Cys
                420                 425                 430

Gly Gly Val Arg Ala Gly Leu Gln Gly Glu Thr Asn Val Leu Gly Leu
                435                 440                 445

Phe Val Ala Gly Glu Val Ala Cys Thr Gly Leu His Gly Ala Asn Arg
450                 455                 460

Leu Ala Ser Asn Ser Leu Leu Glu Ala Leu Val Phe Ala Arg Arg Ala
465                 470                 475                 480

Val Gln Pro Ser Thr Glu Leu Met Lys Arg Thr Arg Leu Asp Val Cys
                485                 490                 495

Ala Ser Glu Lys Trp Thr Arg Pro Val Val Ala Thr Ala Arg Leu Leu
                500                 505                 510

Gly Asp Glu Val Ile Ala Lys Ile Ile Ala Leu Thr Lys Glu Val Arg
                515                 520                 525

Arg Glu Leu Gln Glu Val Met Trp Lys Tyr Val Gly Ile Val Arg Ser
530                 535                 540

Thr Ile Arg Leu Thr Thr Ala Glu Arg Lys Ile Ala Glu Leu Glu Ala
545                 550                 555                 560

Lys Trp Glu Thr Phe Leu Phe Glu His Gly Trp Glu Gln Thr Val Val
                565                 570                 575

Ala Leu Glu Ala Cys Glu Met Arg Asn Leu Phe Cys Cys Ala Lys Leu
                580                 585                 590

Val Val Ser Ser Ala Leu Ala Arg His Glu Ser Arg Gly Leu His Tyr
                595                 600                 605

Met Thr Asp Phe Pro Phe Val Glu Glu Ser Lys Arg Ile Pro Thr Ile
                610                 615                 620

Ile Leu Pro Ser Ser Pro Thr Thr Ala Ser Trp Ser Ser Arg Arg Leu
625                 630                 635                 640

Gln Asn Ile Ser Ser Ser Ser Leu Ile Asp Cys
                645                 650

<210> SEQ ID NO 3
<211> LENGTH: 1953
<212> TYPE: DNA
<213> ORGANISM: Populus trichocarpa

<400> SEQUENCE: 3
atgacaacga gtatagctgg tggaagcagc aacctccact accggttaag tttccgccag      60
gctaaaggtt gtagacaatc ttcttggatt tccagtttga cattcaatgg atgcttgcgg     120
```

-continued

```
aatgagattt catggtcgga tgggctatca aagttgttgc agttccagag atataaattt      180
tcccgatcta ccattagcaa aaactggaaa cctcttggaa caagaaaagt aagtgtatca      240
tcttgcttga gagatagtac agttaagtac tttgattttg ctgtcattgg aagtggagtt      300
gctggtctgc gctatgctct tgaagttgca aaatatggaa ctgttgcagt cattaccaag      360
gctgagcccc atgagagcaa tacaaactat gcccaaggtg gtgttagtgc agtgctgtcc      420
ccatcagact ctgtggagag tcacatgcag atactatgg tagcaggtgc ttatctatgt       480
gatgaggaga ctgtcagagt tgtctgcaca aaggacctg acagaattag agaattgata       540
gctatgggtg caatgtttga tcatggggag atggaaact tgcacctagc aagggaaggg       600
ggtcactctc accatagaat tgttcatgct gctgatatga ccggaaggga gattgagcga      660
gctctgctgg aggccgttgt caatgatcct aatatctctg tgtttgagca ccattttgcc      720
atagatttgc taacttctca ggatggtcct gacatggttt gtcatggtgt ggacactttg      780
aacactgaaa ctcaacaggt ggttcgattt atttcaaagg tgactttact tgcatcaggt      840
ggggctgggc atatctaccc atccaccaca aatcctccgg tggcaacagg agatggaatg      900
gctatggctc accgagctca agctgtgatt ccaacatgg aatttgtgca gttccaccca       960
actgctttag ctgatgaagg gcttcccata aaaccaatca agctcgaga aaacgcattt      1020 ctcatcactg aagctgtaag gggcgatgga ggcatcctct ataacttaga ctgggaaaga     1080
ttcatgcccc tgtatgatga gagagctgag ctagctccta gggatgtagt ggcgaggagc     1140
atagatgacc agcttaagaa gcgttgtgag aagtatgtgc tacttgatat tagtcacaag     1200
cctagagaga agattctctc tcacttcccc aacatagctg ctgagtgcct ccagtatggc     1260
ctggatataa cccgccaacc aattcctgtg gttcctgctg cccattacat gtgcggtgga     1320
gtccgtgctg ggcttcaggg ggagacaaat gtgcagggcc tctatgtggc aggtgaggtt     1380
gcatgcactg gtttgcacgg agcaaaccga ctcgctagca attcattgct ggaagcacta     1440
gtttttgctc gaagagctgt tcagccatca attgatcaca tgaagagctc tagccttgat     1500
ctcagtgctt caaattggtg ggccagacca gtagtaccca attcacctgg gagcaatgta     1560
atggacaacg tatcgaggaa gacaagggaa gtgaggagag agttgcagtc aatcatgtgg     1620
aagtacgtag ggattgtccg gtcaacaaca aggcttgaaa ccgcggaggg agaaatcagt     1680
gagttagagg cccagtggga gaagtactta ttcgaggaag gatgggagca gacaatggtg     1740
gggcttgagg cttgtgaaat gagaaacctc ttttgttgtg caaagctggt agtgagcagt     1800
gcactcgcta ggcatgaaag ccgtgggctg cactatacga ttgattttcc tcatgtggag     1860
gaaagtaaga ggctaccaac agttattctt ccatctcttg tgaataataa tacatggagc     1920
tcacgacagc tacacaagca ggtcattttt tag                                  1953
```

<210> SEQ ID NO 4
<211> LENGTH: 1929
<212> TYPE: DNA
<213> ORGANISM: Solanum lycopersicum

<400> SEQUENCE: 4

```
atggcaactg gtatagcttc aggaagcggg caattatatt tgagggagca tgtctatcgg       60
aggagtagct atggaaaagc tcattgtcat tccactgtga tcctgagcag catgcaaaac      120
caaatccatt ggtcttcttg gatttccaaa ctcttacaag ttgatagaag taactattca      180
caatgtcaag tgaaaacaaa ccggaagtct cacagaggaa caatcaaatc atgccagaga     240
```

-continued

```
gaaggctcaa caaggtattt tgattttgct gtgattggta gtggcattgc tggccttcga       300
tatgctcttg aggttgccaa acatggatct gtggctgtga taaccaaggc cgagcctcat       360
gagagtaaca ctaactatgc tcaaggtggt gtaagtgctg tgctctgccc taaggattca       420
gtggagaacc acatgaaaga tacaattgtg gcaggtgctt acctctgtga tgaggagatt       480
gttagagttg tgtgcactga aggacctgag agaattagag aactgattgc tatgggtgct       540
tcgttcgatc atggggagga tggcaatctg catctagcca gggaaggggg ccactcccat       600
cgccgaattg tccatgctgc tgatatgaca ggcagagaga taggaagggc cctattagag       660
gcggttgtta aggatcctaa tatatatgtg tttcaacacc attttgcaat agatttgttg       720
accacccagg atggttctga catagtttgt cacggaattg atactataaa cacagaaaca       780
caggaggtca taagattcat ttcaaaagtg actttgctgg catcaggtgg agctggacat       840
atctatccaa gcactactaa tccgccagtt gccactggag atggaatagc tatggctcat       900
cgagctcaag ctgtaatttc caacatggag tttgtgcaat ccacccgac tgccttggct        960 gatgaaggcc ttcccatcag accatcaaat gccagagaga atgcttttct gataactgaa      1020
gctgtcagag gtgatggagg cattctttac aacttagata tggagagatt catgccatcg      1080
tatgatgaaa gagccgagct tgccccaaga gatgtggtag caagaagtat tgatgaccag      1140
ctcaaaaagc gtggtgaaga gtatgttctt cttgatatca gtcacaagcc caaagagaag      1200
attctttctc atttttcctaa catagctgct gagtgtctcc gctatgggtt agacataaca      1260
cagcagccga ttccagtggt tcccgcagct cactacatgt gtggtggagt ccgtgctggg      1320
ctcgaaggtg agactaatgt acgaggtctt tatgtggcag gtgaagttgc atgtactggt      1380
ttgcatggtg caaaccgact tgctagcaac tccttggctg aagcactagt gtttgcacga      1440
agagctgtaa agccttcaat agatcacatg aaccttt cta aaatcggtca cagtgcttca      1500
aattggtggc cgcggcctgt agcacccttg ttactaggag atacagtagt taacaaagtc      1560
attcgtcaga caagggaagt gaggaaagaa ctacagtcaa tcatgtggga atacgttgga      1620
attgttcggt ctacctcacg actaacccct tgcagaaacca gaatcataga gttggagtta      1680
aaatgggaac gataccctat tcagcatggg tgggaaccga ctatggttgg tttagaggct      1740
tgcgagatga ggaatctctt ctgttgtgcc aagctggttg ttagcagtgc cctttcgcga      1800
catgagagtc gtgggcttca ttataccatt gacttccctc acgtcgagga aagcaagagg      1860
ttgcctacag taattttttcc ttcacagcta aatagctcgc ggcaattaca taagcagcag      1920
atatgttag                                                              1929
```

<210> SEQ ID NO 5
<211> LENGTH: 1944
<212> TYPE: DNA
<213> ORGANISM: Glycine max

<400> SEQUENCE: 5

```
atggcaactt gtgttcctgc tgtaagtggt gcactgcatt atggagtgac aaactgcaag        60
ggacacagct acagaaggag tgcttccttt tctgatgtgc taacacggg attcttacaa        120 aaagatcttt catggtctaa agtggtatcc aaggtcctgc agatacacag atgtgggttt       180
tctgcaccct cacttcataa ggatcagaaa ctcttcaaag tcatttcctc atggaagaaa       240
gatagtccca caaatactt tgactttatc gtcattggga gtggaattgc tggcctccga       300
tatgcgctta agttgcaaa atatggatct gttgcagtga taaccaaggc tgagtctcat       360
gaatgcaata ctaattatgc tcaaggtggt gttagtgctg tgctatgccc ttcagattct       420
```

-continued

```
gtggagagtc acattaagga caccattgtg gctggggcat atctttgtga tgaggaaagc      480
gtccggsttg tctgcactga aggacccgaa agagtcagag aactgattgc tatgggtgca      540
tcatttgatc atggggaaga tggtaacttg catctaatga gagaggggggg tcattcacat     600 catagaattg ttcatgctgc tgatatgact ggaaaagaga ttgaacgggc tctactgaag      660
gaagttatca gtaatcccag aattttttgtg tttgaacacc attttgctat agatcttctc     720
acttgtcagg atcgatctga tatgatttgt cttggtgttg acacactgaa ttctaaaacc      780
ctagaggtga ttagatttct ttcaaaggtc acttacttg cgtcaggtgg agctggacat       840
atttatccta aaactacaaa tcctctggta gccactggag atggaattgc catggcacac     900
cgagctcaag ctgtgatttc aacatggag tttgtgcagt tccatccaac tgccttagct      960
gatgaagggc ttcctattaa accaaccaag cctcgggaaa atgcatttct gataactgaa      1020
gctgtcagag gtgatggggg catcctttat aattttggca tggaaagatt catgcccttg     1080
tatgatgaga gggcagagct tgctccaagg gatgtggtgg caagaagtat agacgaccaa      1140
cttaaaaagc gtcatgagaa gtatgtgctc ctcgatataa gtcacaagcc caaggaggaa     1200
attctctccc atttccccaa cattgcttct acgtgtctcc agtatgggttt ggacataact    1260 cgtcgtccaa tcccagttgt tccagctgct cattacatgt gtggaggagt tcaagctggt     1320
ctccaaggag agaccaatgt gaaaggtctg tatgtagctg gtgaggtagc atgcacaggt    1380
ttgcatggag caaatagact tgctagcaac tcattgcttg aggcactggt ttttgcaaga     1440
agagctgtgc agccctcagt tgatcacatg aagggctcta gccttgatct gactgcatca     1500
aacttgtggc ctagacccgt tgtgcctttg ccactcggaa gtaatgtcac agacaaaatt     1560
atgtcaacga caaggaatt gagggcagaa ctgcaatcca tcatgtggga ctatgtagga     1620
attgttcggt ccacaatgag actagagact gctgagcaaa aaattggtag tttagaagct     1680
aaatgggagg agtctctgtt tcagcatgga tggaagccaa caatggtcgg gcctgagatc     1740
tgtgagatga gaaacctctt tgttgtgca aagctggtgg tcagcagtgc gctttctagg     1800
catgagagcc gtggactaca ttacactgtt gattttcctt atctcgagga gagtaagaga     1860
cttccaacaa tcatttttcc aagttcacct gtaaacagta catggagttc tcggcaatta     1920
cacaagcagc ccatgtacca gtaa                                            1944
```

<210> SEQ ID NO 6
<211> LENGTH: 1938
<212> TYPE: DNA
<213> ORGANISM: Oryza sativa

<400> SEQUENCE: 6

```
atggcggctc tgatgaacgg ctttgggagc ctccaatgca aggcgacggt gcatgtcgag      60
aaagggcaca tgcaagcatc ggggatggcc ttcttctctc ccgtcaacag atgcgcccag     120
gttcatatct ccagtattcc tcatttcatc ggcgcgaagt ctgttagtgc ttcccaactt      180
cgaatgaggc acaaggtcgg gtccatcaga gcctctgcag cctcgtgctt gcaagatgaa     240
acaacaaaat atttcgattt tgtggtcatt ggcagcggtg ttgctggcct aaggtatgct     300
ctggaagtgt ctaagtacgg ctctgtcgcc atcattacca aagcagagcc tcatgagagc     360
aacacgaact acgcacaagg cggtgtcagc gcggttctat gcccctcaga ttctgtagag      420
agccacatgc aagacaccat tgtcgcgggg gcttatctgt gtgatgaaga gactgtcagg     480
gtagtatgca cagaaggacc ggagcgtgtg aaggagctca ttgccatggg agcttcattt     540
```

```
gaccatggcg aggacggaag gctgcacctt gcaagggaag gtggacattc tcacaacaga       600
atagttcatt ctgctgatat gactggaaga gagatcgaga gagcactgct tcaagcagtt       660
gataatgatg ataacatatc tttgtttggc caccactttg ccattgattt actcacctgt       720
cagagtaatg tgtgaaatata ttgctatggt gtggattcat ggacgctga aactcagaag       780 gcaattcgtt tcatctcgaa agtaacattg cttgcatctg gaggagttgg tcatatatac       840
ccctcaacga ccaatccacc ggtagctact ggggatggaa ttgcaatgtc tcatcgtgcg       900
caggctgtaa tatctaatat ggagtttgtg cagttccacc caactgcact atcagatgag       960
ggtctcccaa taaaaccagc tacaagaaga gagaatgcat tcctcataac agaagcagtc      1020
agaggagatg gaggaattct ttataatcag tccatggaga ggtttatgac ttcgtatgat      1080
gaccgtgcag agttagcacc gagagatgtg gtcgcaagaa gcatagatga ccaactgaag      1140
aagaggggag aaaagtatgt cctcctggat atcagtcaca agccaaggga aaaggttctt      1200
gcccattttc caaacattgc agctgaatgc ctgcgccacg gtctcgacat cacacaacag      1260 ccgataccctg ttgttcctgc agctcattac atgtgtgggg gtgtccgggc tgggttgcag      1320
ggggagacaa atgtgaaagg cctgtatgtt gctggtgagg ttgcatgcac tggattgcac      1380
ggtgctaatc ggcttgcaag caactcactg cttgaagcac tggtgtttgc tcggagagca      1440
gtgcagcctt caatagatca tatggtcgat gcagatgtcg atccttcttt cgcgaagaaa      1500
tgggctcgtc ctgtgctgtc tgtctcccctt agggacagta tactatctga tatcattgag      1560
aagacaaagc aggccaggat ggagcttcag tcaataatgt gggagtatgt cgggatagtg      1620
cggtcgacga accgcctgaa gcacgcggaa tggaagatca gtgatctgga gtcagaatgg      1680
gaggagttct tgttcaggag ggggtggaag cctacaatgg tgggggttga gacctgtgaa      1740
atgaggaacc tcttctgctg cgcaaagctg gttgtgaaaa gtgctcttgc aaggcacgag      1800
agccgaggct tgcacttcac cgaagacttc ccttacctgg aggagagcaa gaggaagcct      1860
acagtgatct tccctactca tatccaggag ctgacatgga gctcaaagcc attgcagaag      1920
cagctgcagt gcaagtag                                                    1938
```

<210> SEQ ID NO 7
<211> LENGTH: 1995
<212> TYPE: DNA
<213> ORGANISM: Zea mays

<400> SEQUENCE: 7

```
atggcgaacc tgacgaacgg ctttgcgagc ctccattgcg cagggggcgat gcatgtggac        60 aaagggcaca tgcaagcatc gggactgcct tttctctctt tcagaagatg cgcccagctt       120
gatatctcca gactaggtag cgtgcctcgt ttcatgggcg caacatctgc tactgtctcc       180
caacatcatg tgaggcagag gatcagcgcc atcagagcct ctactctttc ctgcctgcaa       240
gacgatgcca caaattctt tgattttgtg gttattggca gcggtgttgc tggcctaagg       300
tatgctctgg aagtttcaaa gcacggctct gttgctatta tcaccaaggc agagcctcat       360
gagagcaaca caaactatgc acaaggcggt gttagtgccg ttctatgccc ctcggattct       420
gtagaaagtc acatgaaaga cacaattgtt gcagggcct atttgtgcga tgaagagatt       480
gtcagggtag tttgcacaga aggtccagag cgtgtcaagg aactaattgc catgggtgcc       540
tcattcgacc atggtgaaga tggtaggctg caccttgcaa gggaaggtgg tcattctcac       600
aacagaattg tccattctgc cgatatgact ggaagagaga ttgaaagagc actgcttcaa       660
gcagttcaca atgatgataa catatctttg tttggtcatc actttgctat tgatctattg       720
```

```
acatgtcaga aaaatggtga aatctattgc tatggagtgg attcaataga cattgaaacc      780
cagaaggtag tccgcttcat ctcgaaagtg acattgcttg catcaggagg agctggccat      840
atatatccca caaccaccaa tccaccggta gctactgggg acggaatcgc aatgtgtcat      900
cgtgctcagg ctgtaatatc caatatggag tttgtgcagt tccatccaac tgcactttca      960
gatgagggcc tgccaataaa gccaaagaca agaagagaga atgcatttct cataacggaa     1020
gcggtgagag agacggagg aattctttac aaccagtcca tggagagatt catgccgatg      1080
tacgatgacc gctcggagct ggcgccgaga gacgtggttg cgaggagcat agacgaccag     1140
ctgaagaaac gaggcgaaaa gtatgtcctc ctggacatca gccacagacc aagagacaag     1200
gttcttgccc acttccccaa catcgccgcc gagtgcctgc ggtacggcct ggacatcacc     1260
cggcagccca tcccggtggt cccggcggcg cactacatgt gcggcggcgt ccgggcaggg     1320
ctgcagggg agaccaacgt gaagggcctc tacgtggccg gcgaggtcgc gtgcacgggg     1380
ctgcacggtg ccaaccggct agcaagcaac tcgctgctgg aagcgctggt gttcgccagg     1440
agggcggtgc agccgtccat cgacctcatg gtggatgccg acggagatgc cagaccgtcg     1500
ctggtggcga ggtgggcacg gccgacgctg ccgcggtcgg tgctgggcga cagcgtgctg     1560
tcggacatcg tggggcggac gaggcaggcc aggatggagc tgcaatcagt gatgtgggag     1620
tatgtcggca tcgtgcgctc gacggggcgg ctgaagcagg ccgagtggag gatcggtgac     1680
ctggagtcgg agtgggagga gttcctgttc cggcgggggt ggaagccgac cacggtgggc     1740
gtcgaggtct gcgagatgcg caacctcttc tgctgcgcca agctcgtcgt caggagcgcg     1800
ctggccaggc gcgagagccg cggcctgcac ttcaccgagg acttcccgta cctggaggag     1860
agcaggagga agcctacggt catcttcccg gccgccgtgc aggagctcac gtggagctcc     1920
aagccgttgc agaggcagct gcaagcagat gacaatgcat gcagttcatc cggctgggcc     1980
ttggggattc gttaa                                                      1995

<210> SEQ ID NO 8
<211> LENGTH: 1965
<212> TYPE: DNA
<213> ORGANISM: Sorghum bicolor

<400> SEQUENCE: 8
atggcgaacc tgacgaacgg ctttgcgagc ctccattgcg caggggcgat gcatgtggac       60
aaagggcaca tgcaagcttc gggactgcct tttctctctt tcagaagatg ctccaagctt      120
gatatctcca gactaggtac cgtgcctcgt ttcatgggcg caaaatctgc tactgtctcc      180
cagcatcatg tgagacacag gatcagcgcc accagagcct ctacttttc ctgcctgcaa      240
gatgatacca caaaattctt cgatttcgtg gttattggca gtggtgtcgc tggcctaagg      300
tatgctctgg aagtttcaaa gcacggctct gttgctatta tcaccaaggc agagccttat      360
gagagcaaca caactatgc acaaggcggt gttagcgccg ttctatgccc ctcggattct      420
gtagaaagtc acatggaaga cacaattgtt gccggggctt atctgtgtga cgaagagacc      480
gtcagggtag tttgcacaga aggtccagag cgtgtcaagg aactaattgc catgggtgcc      540
tcattcgacc atggtgaaga cggtaggctg caccttgcaa gggaaggtgg acattctcac      600
aacaggattg tccattctgc tgatatgact ggaagagaga ttgaaagagc actacttcaa      660
gcagttgaca atgatgataa catatcgttg tttggtcatc acttgctat tgatctattg      720
acatgccaga aaaatggtga aatatattgc tatggagtgg attcgataga cattgaaact      780
```

```
cagaaggtag tccgtttcat ctcgaaagtg acactgcttg catcaggagg agttggccat        840
atatatccca caaccaccaa tccactggta gctacagggg atggaatcgc gatgtctcat        900
cgtgctcagg ctgtaatatc caatatggag tttgtgcagt tccatccaac tgcactttca        960
gatgagggcc tgccaatcaa gccaaagaca agaagagaga atgcattcct cataacggaa       1020
gcggtcagag gagacggagg aattctttac aatcagtcca tggagagatt catgcccatg       1080
tacgacgatc gcgccgagtt ggcgccaaga gatgtggttg cgaggagcat agatgaccag       1140
ctgaagaagc gaggcgagaa ctacgtcctc ctggacatca gccacaagcc aagagagaag       1200
gttcttgctc acttccccaa catcgccgcc gagtgcctgc ggtacggcct ggacatcaca       1260
cggcagccca tcccggtggt cccggcggcg cactacatgt gcggcggcgt ccgggccggg       1320
ctgcaggggg agaccaacgt gaagggcctg tacgtcgccg gcgaggtcgc gtgcacgggg       1380
ctgcacggcg cgaaccggct ggcgagcaac tcgctgctgg aggcgctggt gttcgccagg       1440
agggcggtgc agccgtccat cgaccacatg ttggacgccg acggcgacgg cgacggcgac       1500
ggcgacgctt ccctggcggc gagatgggcg cggccgacgc tgccgtggtc gtcgctgggc       1560
gacggcgcgc tgtcggacat cgtggagcgg acgaggcagg ccaggacgga gctgcagtcg       1620
gtgatgtggg agtacgtcgg catcgtgcgg tcgacggggc ggctgaagca ggccgagtgg       1680
aagatcggcg acatggagtc ggagtgggag gagttttgt tccggcgggg gtggaagccg       1740
accatggtgg gcatcgaggc ctgcgagatg cgcaacctct tctgctgcgc caagctcgtc       1800
gtcaagagcg cgctggccag gcgcgagagc cgcggcctgc acttcaccga ggacttcccc       1860
tacctggagg agagcaggag gaagcccacg gtcatcttcc cggccgccgt gcaggaggtc       1920
acgtggagct ccaagccgtt gcagaggcag ctgcagtgca agtag                      1965

<210> SEQ ID NO 9
<211> LENGTH: 2010
<212> TYPE: DNA
<213> ORGANISM: Chlamydomonas reinhardtii

<400> SEQUENCE: 9
atggcagtcg cgcttcagcg ctctgctgtg ggtaagcgcc tgcgcgccgc taccccggtc         60
cgcgtcggcc tgagcgagtc ggctcggcga cctgtggcgc gccccactgg tgtggccgct        120
cgtcgggtca cccgcagctt cgtcgtccgc gctgacgtga actccgatgc gttccagcca        180
cgcccggcgg gcgccccggc cgcgcgtgtc gcgcccgaga cacgccgcc tgtccgtcaa        240 cacgatttcc tcgtcatcgg ctcgggcatc gccggcctga cgtacgcgct gaaagtggca        300
gagtatggca cggttgccat catcaccaag gacaacgctg ctgagggctg cactcggtat        360
gcgcaaggag gcgtgtgcgc tgtgctggac aagagcgaca gtgttgctga tcacgttcgt        420
gacaccattg ttgctggcgc cttcttgaac gatcctcagg ccgtggaagt tgtgtgccgt        480
gagggccccg cccgcgtgct ggagctggtg gagctgggcg ccgagttctc ccgcaacaac        540
gatggctccc tgcacctgac caaggagggg ggccacagca accgcggat cgtgcacgcc        600 gcggatatga cgggcgcaga gatcgagcgc gcgctgctga cgtccgccaa gagccaccgc        660
aacatccact ctatgagca ccacctggcg gttgacctag tcgtggacga gtatggtggt        720
atgctgcact gcttcggcgc cgacgtgctg accagcgtt ccggcacgat gagcaggttc        780
ctgggcctgg ccacgctgct ggctagcggt ggcgctggtc aggtgtaccc caacaccacc        840
aacccgcacg tcgccaccgg agacggcatc gctatgcct accgcgcgca cgccaacgtg        900
agcaacatgg agttcgtgca gttccacccc actggcctgt acaaccccgc cggtggtgag        960
```

```
ggcagcacct tcctgatcac cgaggccgtc cgcggcgagg gcggtatgct gttcaacaag    1020
gccggcgagc ggtttatgga gacgtacgac aaggagcgcc tggagctggc cccgcgcgac    1080
gtggtggcac cgccattca cgaccagatg cgcctgggca cgagcacgt gtggctggac      1140 atcagccaca agcctcgcga tgaggtgcta caccacttcc ccaacatcgc ggcgcgctgc    1200
cttaccctgg gtatcgacat cgccgctgac cccatcccgg tggtgccggc gcagcactac    1260
acgtgcggcg cgtcaacac gggcctgctg gcgagacca atgtgcaggg gctgtacgcg      1320
tgcggcgagg tggcctgctc cggcctgcac ggcgccaacc gcctggcttc caactctctg    1380
ttggagggcc tggtgtttgc agagcgtgcc gtcaaccca gcgtggcgca cgctgagcac     1440
gcgctgcgca actgcggccg gcagctgcac tacgccgctg ccagcgcgga tttccgcggc    1500
gcgcgtggcg cgcggggagct gacgcccgag ctggcgcagt gggtgtcggc gcggcgtcaa   1560
gagctgcgcg acatcatgtg gcgctactgc ggcatcgtgc gcaggaccaa ggagctgcag    1620
caggcccgcg acttcgtggt gtcgctgtac attgagacga aggccatcta caagaactac    1680
ggcgtgaaca cgcagttggt ggagctgctc aacatggcca ccgtggcgga gctgacggtg    1740
tcgtgcgcgc tgcagcgcaa ggagagccgg ggcctgcact ttagcgccga ctacccgcac    1800
ctggacgacg cgcagcgccg ccccagcatg atcagcacct cgctcaagac gcgctacgac    1860
ctgtcgccct acatgcgcaa cgtgccatct gtgctgcccg ccggggctgg cggcccgca    1920 agcccggcgc agggcaagcg cctggcgccg cgcaagcagc ccacccgcga gcgcgagttg    1980
gcggtgcgct ccacgccgca agacctgtga                                     2010

<210> SEQ ID NO 10
<211> LENGTH: 2004
<212> TYPE: DNA
<213> ORGANISM: Phaseolus vulgaris

<400> SEQUENCE: 10
atgcagtcgc ctacttgtat tgcaatggcg acttggatac ctgctggaag tggcacactg    60
caatttagag tgacaaactg caagggacac agttgtagaa ggactgcttt ggtttctgat    120
gccccaatcg cgagattctt acgaaaagat ctttcatggt ctaaagcagt atccaaacac    180
gtttgtgcat ttctgcacc tccacttcaa aagaatcaga aactcttcaa atcgtttcc     240 tcttgcaaga tagatagtct cacacagtgc tttgactttt ccattattgg gagtgggatt    300
gctggtctcc gctatgcgct tgaagttgca aaatatggat ctgttgcagt gataaccaag    360
gctgagtctc acgaatgcaa tactaattat gctcaaggtg gtgttagtgc tgtgctaggc    420
ccttcagatt ctgtggagag tcacatgaag gacaccattg tagctggggc atatcttttgt   480 gatgaggaaa gcgtccgagt tgtctgtact gaaggacctg aaagagtcag agaattaatt    540
gctatgggtg catcatttga ccatggggaa gatggtaact tgcatcttat gagggaggga    600
ggtcattcac atcatagaat tgttcatgct gctgatatga ctggaaagga gattgaacgt    660
gctctactga aggcagttat caacaatcct aatatttttg tgtttgaaca ccatttgct    720 attgatcttc ttacttgtca ggatgaatct gacataattt gtcttggtgt tgacacgctg    780
aacactaaaa ccctagaggt gggaacagca gtgataagat ttctttcaaa ggcgacttta    840
cttgcatctg gtggagcagg gcatatttat cccaaaacta caaatcctct ggtagccact    900
ggagatggaa ttgccatggc tcatcgagct caagctttga tttccaacat ggagtttgtt    960
cagttccatc caactgcctt agctgatgaa gggcttccta tcaaacaaac caagcctagg    1020
```

```
gaaaaagcat tctctgatatc cgaagcggtt agaggtgatg ggggcatcct ttataattta      1080
ggcatggaaa gattcatgcc cttgtatgat gagagggcag agcttgctcc aagggatgtt      1140
gtggctagaa gcatagatga ccaacttaaa aagcgtgatg agaagtatgt tcttcttgat      1200
ataagtcaca agccgaagga ggaaatcctc tcccattttc ccaacatttc atctacgtgt      1260
ctcaagtatg gtttggacat aactcgtcac ccgatcccgg ttgttccagc tgctcattac      1320
atgtgtggag gagttcaagc tggtcttcaa ggagagacca atgtgaaagg tctgtatgta      1380
gctggtgagg tagcatgcac aggtttgcac ggagcaaaca gacttgctag caactcattg      1440
cttgaggcac tcgttttttgc aagaagagct gtgcagccct cagttgattg gatgaagagc      1500
tctagccttg atctgactgc atcaaacttg tggcctcgac ctgctgctgc gcctttgtcg      1560
ctcgaaagta atgtcactga caagattctg tcaatgacaa aggaatcgag acagaactg      1620 caatccatca tgtggaacta tgtaggaatt gttcggtcga cgatgagact agagacagca      1680
aagcaaaaca tttgcaactt ggaggctaaa tgggaggagt gcttgtttga gcatggatgg      1740
aagccaacaa tggcaggtcc tgagatctgt gagatgagaa acctcttttg ctgcgcaaag      1800
ctggtgatca gcagtgctct tcgaggcac gagagtcgag gactgcatta cacagttgat      1860
tttcctcatc ttgaggaaag caagagactt ccaacaatca tttttccaag ttcaactgta      1920
aacagtacat ggagttctcg acaattacac aagcagccca tgtaccagga aggcatcaaa      1980
ttgtgtcaca atacatataa atag                                             2004

<210> SEQ ID NO 11
<211> LENGTH: 1863
<212> TYPE: DNA
<213> ORGANISM: Physcomitrella patens

<400> SEQUENCE: 11
atgttttttt tgaacgctat tccgataaat ctctgtggtg ttttcttgca gctaaacggg        60
cgggacagga gaaatgaaat tagaaagttt attgccgcct cgaatcgtaa catccaggca       120
gaagcgagct tatctggtga tggcgaagag gaggagatca cgaaatactt cgatttcctc       180
gtaatcggaa gtggaatagc aggcttgaga tatgctctgg aagttgccaa gtacggttca       240
gttgcaatac tcacgaagtc cgaaccgcac gagagtaaca ctgtgtatgc acagggaggt       300
gttagtgctg ttttagatcc cgaagattct gtagagagtc acatccgaga cacgatcgtc       360
gctggtgctt tcttatgtga tgaggagact gtagaggtcg tgtgtcgaga aggtccagag       420
cgtgtgaaag agttgatggc ttggggtgca ttgtttgatc aaagtgaaga tggtcagctc       480
catctagcta gggaaggagg ccactctcat catcgcattg ttcatgcggc tgatatgact       540
gggcgagaga tcgagagagc tcttttgact accgtttctc aaaatccgga cattgtaatt       600
tttaaacatc atgctgctgt ggatcttctc actcttcagg acggggacag tgtagtatgc       660
tatggtgtgg atgctctaga tacgcagaaa aataaagtta tgcgttttct agccggagtt       720
acgatgttag catcaggagg tgcagggcac gtttatccta ctacgaccaa tcctttggtg      780
gcaaccggcg atggagttgc tctggcacaa cggtctcgtg cagtggtgtc taacatggaa      840
tttgtacagt tcatcccac ggctttggcg gatgaaggct taccaataaa acctgccaaa      900
cgggacaatg catttctgat tacgaagct gtgcgtggag ctggaggaat tttgtataac      960
caaagtatgg agagatttat gccattatat gactctcgcg cggagctcgc acctcgggat      1020
gttgtggccc ggagcattga tgatcaactc aagaaacgta atgagaaatt cgtttatctg      1080
gatatcagcc ataaaccagc cagcgagata atgtctcact ttccaaatat tgctgctgag      1140
```

```
tgcctgaagt atgggctgga tattacgaag caacccatcc ctgtggtacc tgctgcacat    1200
tacatgtgtg gaggcgtaca gactggtttg gtgggagaga cctcaatcaa ggggctcttt    1260
gccgctggtg aagttacttg taccggtttg cacggtgcaa atagacttgc cagcaattcc    1320
ttactggagg ctttagtgtt tgcgagagag ctgtcgagc cttcagttgc ttacgcactt     1380
cagagtaaca ttggacgatc ggaggtgaag caagcgaagg agtggcctcg tcctactgct    1440
ccctcagctt caaatgactt gcagatggat gagattctcc gcattacagc tttgaaaagg    1500
aagcgattgc aacaagcaat gtgggatttt gtcggaattg ttcggtctac agagcgtctc    1560
aagcgtgctc aagcggagtt aagggagctg gagtgtgaat gggaggcaca actcctcaga    1620
catggttgga aacctaccat ggtcagctta gaggtttgtg agatgcgcaa cttggtatcg    1680
gtgtcctacc tgattgtgaa cagcgctctc acacggcaag agagtcgtgg ccttcattac    1740
acgacaagct ttccagaact tgttgagagc gaaaggtttc ctaccattct ttgtccgacc    1800
gctgcaatga caattcgtg gagttcacag gttgttcaca gattggcaat agaatctcaa      1860
taa                                                                  1863
```

<210> SEQ ID NO 12
<211> LENGTH: 1602
<212> TYPE: DNA
<213> ORGANISM: Rhodothermus marinus

<400> SEQUENCE: 12

```
atgcccgagc gttatcagtt cgatttctg gtcatcggta gtggcattgc cggcctgacg      60
ttcgcgctgc gcgtggccga tcacggctcg gtcgccatcg tcacgaaaaa agaaagcgtc    120
gagtcgaaca cgaactacgc gcagggcggc attgcggccg tcatggacgc ggccgattcg    180
ttcgaacagc acgtgcagga tacgctcgaa gccggggccg gcctgtgcga ccgcgaggtg    240
gtggaaacgg tcgtgcggga agggcccgaa cgggtgcgtg aactgatggc gctcggggca    300
cagttcaccc gcgaaaacgg ccggctgcat ctggggcgtg agggcggcca ctcccggaat    360
cgcatcgtgc acgccgccga cgcgaccggc cgcgaggtcg agcgggcgct gctggcgcgc    420
gtgcgcgccc acccgaacat tcacatcttc gagtaccatt atgcggttga tctgatcacc    480
gagcatcatc tcggccagta cgtctcgcgg ttgcgtcccg acatccactg cttcggggcg    540
tacgtgctgg acgagcgggc cgacgtggtg catacgtttc tggcgaaggc cacccctgctg   600 gccacgggcg gttccgggca ggtctacctg cataccacga acccgccggt ggccacgggc    660
gacggggtgg ccatggccta tcgggccaag gcccgcgtgg ccaacatgga attcattcag    720
tttcacccga ccacgctttt ctaccccgac ggtcccaagg aacgctcgtt tctgatcagc    780
gaagcggtgc ggggtgaggg agcccggctc tacaacctgg ccggcgagcg cttcatgccg    840
aagtatgacc gcgggccgga gctggcgccg cgcgacattg tggcgcgcgc catcgacgac    900
cagctcaagc ggcgcggcga tccgcacgtc tggctggaca tctcgcaccg gccggccgag    960
gaaatcaaac gccgcttccc gaacatctac cggacgctgc tcgactacgg catcgacatg    1020
acacagcagc ccattccggt cgtgccggcc gcgcactacc agtgtggtgg cgtactgacc    1080
gacctgcacg tcgcgcaccac gattcatggt ctgtacgcag ccggcgaggt agcctgtacg    1140
ggactgcacg gcgccaaccg actggccagc aactcgctgc tggaggcgct cgtctttgcc    1200 cgacgggcg ccgaagacgc cgtgcagtac atccagacgc agacgtggcg tacgacgtg     1260 ccggactggg acgaccgggg caccgagcgc ccgcaggaat gggtgctcat cgcgcacaac    1320
```

| | | |
|---|---|---|
| cgggacgagc tgcggcgcat catgtgggac tacgtgggca tcgtgcgctc gcagcttcgt | 1380 |
| ctggagcggg ccctgcgccg cacccgactg ctctacgaag aaaccgagga cttctaccgt | 1440 |
| cgcgcccgac tctcgccggg gctgtgtgaa ctgcgtaaca tgatcgccgt ggcttacctg | 1500 |
| atcattcgca cgctctgat cgccgcgag agccgcggct tgcactacat gctcgactat | 1560 |
| ccggagcccg tcgagagcga gcgccggccc acgctggtct ga | 1602 |

<210> SEQ ID NO 13
<211> LENGTH: 1623
<212> TYPE: DNA
<213> ORGANISM: Escherichia coli
<400> SEQUENCE: 13

| | | |
|---|---|---|
| atgaatactc tccctgaaca ttcatgtgac gtgttgatta tcggtagcgg cgcagccgga | 60 |
| ctttcactgg cgctgcgcct ggctgaccag catcaggtca tcgttctaag taaaggcccg | 120 |
| gtaacgaaag gttcaacatt ttatgccag ggcggtattg ccgccgtgtt tgatgaaact | 180 |
| gacagcattg actcgcatgt ggaagacaca ttgattgccg gggctggtat ttgcgatcgc | 240 |
| catgcagttg aatttgtcgc cagtaatgca cgatcctgtg tgcaatggct aatcgaccag | 300 |
| ggggtgttgt ttgatacccca cattcagccg aatggcgaag aaagctacca tctgactcgt | 360 |
| gaaggtggac atagtcaccg tcgtattctt catgccgccg acgccaccgg tagagaagta | 420 |
| gaaaccacgc tggtgggcaa ggcgcagaac catccgaata ttcgcgtgct ggagcgcagc | 480 |
| aacgcggttg atctgattgt ttctgacaaa attggcctgc cgggcacgcg atgggttgtt | 540 |
| ggcgcgtggg tatggaaccg aaataaagaa acggttgaaa cctgccacgc aaaagcagtg | 600 |
| gtactggcaa ccggcggtgc ttcaaaagtt tatcagtaca ccaccaatcc ggatatttct | 660 |
| tctggcgatg gcattgctat ggcgtggcgc gcaggctgcc gggttgccaa tctcgaattt | 720 |
| aatcagttcc accctaccgc gctgtatcac ccacaggcac gcaatttcct gttaacggaa | 780 |
| gcactgcgcg cgaaggcgc ttatctcaag cgcccggacg cacgcgtttt tatgcccgat | 840 |
| tttgatgagc gcggcgaact ggccccgcgc gatattgtcg cccgcgccat tgaccatgaa | 900 |
| atgaaacgcc tcgcgcaga ttgtatgttc ctcgacatca gccataagcc cgccgatttt | 960 |
| attcgccagc attccccgat gatttatgaa aaattgctcg gctgggat agatctcacg | 1020 |
| aaagaacccg tgccgattgt gcctgctgca cattataccct gcgtggtgt aatggttgat | 1080 |
| gatcatgggc gtacggacgt cgatggttg tatgccattg gcgaagtgag ttataccggc | 1140 |
| ttacacggcg ctaaccgcat ggcctcgaat tcattgctgg agtgtctggt ctatggctgg | 1200 |
| tcggcggcag aagatatcag cagacgtata ccttatgccc acggcgtcag tacgttaccg | 1260 |
| ccgtgggatg aaagccgcgt tgaaaacccct gacgaacggg tagtaattca gcataactgg | 1320 |
| cacgagctac gtctgtttat gtgggattac gttggcattg ttcgcacaac gaagcgcctg | 1380 |
| gcacgcgccc tgcggcggat aaccatgctc caacaagaaa tagacgaata ttacgcccat | 1440 |
| ttccgcgtct caaataattt gctggagctg cgtaatctgg tacaggttgc cgagttgatt | 1500 |
| gttcgctgtg cgatgatgcg caaggagagc cgtggcctgc atttcacgct ggattatccg | 1560 |
| gaactgctca cgcattccgg tccatcgatc ctttctgccg gcaatcatta cataaacaga | 1620 |
| taa | 1623 |

<210> SEQ ID NO 14
<211> LENGTH: 1596
<212> TYPE: DNA
<213> ORGANISM: Bacillus subtilis

<400> SEQUENCE: 14

```
atgtctaaaa agacgattgc agtcatcggt tcagggcgg cggcactttc cttagctgca      60
gctttcccgc cctcatacga agtgactgtt atcacaaaaa aaagcgtcaa aaacagcaat     120
tctgtctatg cacaaggcgg gattgctgcg gccatgcaa aagatgactc gattgaagcc     180
catctggagg atacgttata cgcagggtgc ggccataata atctagctat tgtagcagac     240
gtattacatg atggaaaaat gatggttcaa agcctattgg agcgtggatt tccattcgac     300
cgcaatgaac gaggcggtgt ttgtcttgga agagaagggg cccactcata caaccgcata     360
tttcatgcag gcgagacgc aacaggcagg ctgcttatcg attatttgct caaacggatc     420
aacagcaaaa tcaagttaat cgagaatgaa acggcagcag atttgcttat agaggacgga     480
cgatgtatcg gcgtcatgac aaaagacagc aaagggcggc tcaaggtaag gcacgcagac     540
gaagttgtgc tggctgccgg cggctgtgga aacctgtttc ttcaccatac gaatgatctc     600
actgtcacag gtgacggtct ttctctggct taccggccg gggcggaatt aacggatttg     660
gagtttactc agtttcaccc gacactgctt gtgaaaaatg gtgtttccta cgggcttgtt     720
tcagaagctg tcagagggga aggcggatgt ttagtagacg aaaacggccg caggattatg     780
gctgaacggc atcctttagg tgacctggct ccaagagata ttgtctcacg ggttattcac     840
gaagaaatgg caaaaggaaa tcgcgtttat atagacttca gtgcgatttc tgattttgaa     900
acgcgtttcc ctaccatcac cgctatttgt gaaaagcag ggattgatat ccacagcgga     960
aaaattcctg ttgctccggg aatgcatttc ttaatgggag gtgtttcagt taatcgctgg    1020
ggagaaacga cagtgccggg gctttatgcg attggcgaga cagcatgctc cggtttacat    1080
ggagcaaacc ggcttgcaag caattcttta ttggaagcgc tggtatttgg aaaaagggca    1140
gcagagcata ttatccaaaa accggtttat aacaggcaat atcaatcagg ctagaaacc    1200
agtgtcttct acgaggtgcc ggatatagag gggcatgaac tgcaaagcaa aatgacaagc    1260
cacatgtcta ttctgcggga acaaagcagt ttgattgagc ttagcatctg gcttcatacg    1320
ctgccttttc aggaagtaaa tgtgaaggat atcacaattc ggcagatgga actttctcat    1380
ctatggcaaa ctgcaaagct gatgacgttt tctgcgcttt tgcggagga aagcagaggg    1440
gctcacttcc gcaccgattt tcctcatgct gaggtgagct ggcaaggaag acaaattgtc    1500
catacaaaaa aaggaacgaa gatcagaaaa acgagggga tttggaacaa tgaatcattt    1560
acagctgaaa aaattactga atcacttttt tcttga                              1596
```

<210> SEQ ID NO 15
<211> LENGTH: 1413
<212> TYPE: DNA
<213> ORGANISM: Triticum aestivum

<400> SEQUENCE: 15

```
atgggtgctt catttgatca tggtgaagat ggcaggctcc accttgcaag ggaaggtgga      60
cattctcaca acagaatcgt ccattctgcc gatatgactg gaaagagat tgaaagagcg     120
ctgcttcaag cggttgaaaa tgatgagaac atatctgtgt tcggccacca cttcgccatt     180
gatctgttga cctgtcagaa taatggtgaa atctttttgtt acgagtggga ttcattggac     240
accaaagctc aaaaggtagt ccgtttcatc tcaaaagtaa cattgcttgc gtccggagga     300
gctggccata tatatcccac aacaaccaat ccaccggtgg ctactgggga tggaatcgca     360
atgtgccatc gcgctcaggc tgtgatatcc aatatggagt ttgtgcaatt ccatccaact     420
```

-continued

```
gcactatcag acgaaggcct tccaataaag ccagctaaaa taagagataa tgcatttctt    480
gtaacagaag cagtcagagg agatggagga attctttaca accaatccat ggagagattt    540
atgcctttat acgacgaccg tgccgagttg caccgaggg atgtggttgc aagaagcata    600
gatgatcaac tgaagaaacg tggagagaag tatgttctct ggacatcag ccacaagcca    660 agggagaaaa ttcttgctca ttttccgaac attgcagctg aatgcctgcg cacggtctg    720 gacatcacac agcagcccat acctgtcgtc cctgcagctc attacatgtg cggtggtgtt    780
cgggctgggt tgcaagggga gacgagtgtg aaaggcttgt atgtcgctgg tgaggttgct    840
tgcactggat tgcacggtgc taatcgtctt gcaagcaact cattgctgga gcgttggta     900 tttgctcaga gagccgtgca gccctctatc gaccacatgg tggatgcgga tgctgaccct    960
tgtctcgcgg agaaatgggc acgcctgtg ctctctgtct ccattaagga cagtgcactg    1020
tctgacatca ttgagaggac aaagaagacc aggatggagc tgcaatccat aatgtggaag    1080
tacgttggta tagtgcggtc gacgaaccgg ctgaagaatg cagaatggaa gattggtgat    1140
ctagagtcag agtgggagga attcttattc aggaggggct ggaagcctgc ctcagtgggg    1200
atcgaggcct gcgaaatgag gaacctcttc tgctgcgcaa agctggttgt gaagagcgcg    1260
cttgcgaggc gggagagtcg tggcctgcac ttcactgagg acttccctta cctggaggag    1320
agcaagagga agcctacagt gatcttccct actgctatcc aagagctaac atggagttca    1380
aagccattgc agaggcagct gcagtgcaaa tag                                 1413
```

<210> SEQ ID NO 16
<211> LENGTH: 1923
<212> TYPE: DNA
<213> ORGANISM: Hordeum vulgare

<400> SEQUENCE: 16

```
atgggcggct ctgctggcct ccaccatgtg catgtgcagg agcacacat gcaggcgtct     60 cgcccgcctt ctctctcctt cagagcctgc gcccagctcg agatctccag attttgcact    120
accctctcgt tcatgtccgt gaaggctctc agtgcttcgc aacagcatac gaggcacagg    180
ttcagctcca tcagagcctc tgccctccca tgcatgcagg atgacaccac gagatacttt    240
gatttcgtgg tcatcggcag tggtgtcgct ggcctaaggt atgcgctaga agtctcgaag    300
cacggctctg ttgctatcat caccaaagca gagcctcatg agagcaacac caactacgcg    360
caaggcggcg tcagtgccgt tctgtgcccc aaggattccg tagaaagcca tatgcaagat    420
actattgttg caggggctta tctctgcgat gaggagaccg tcaggatagt atgcacagaa    480
ggtcctgagc gtgtcaagga gctaatagcc atgggtgctt catttgacca tggtgaagat    540
ggcaggctgc acctcgcaag ggaaggtgga cattctcaca acagaatcgt acattctgct    600
gatatgactg gaaagagat tgaaagagcg ctccttcaag cggttgaaaa tgatgagaac    660
atatctgtgt tcggccacca cttcgccatt gatctgttga cctgtcagaa caatggtgaa    720
atcttttgtt acggagtgga ttcgttggac accaaagctc aaaaggtagt ccgtttcatc    780
tcaaaagtaa cattgcttgc atctggagga gctggcccata tatcccac aacaaccaat    840 ccaccggtgg ctactgggga tggaatcgca atgtgtcatc gcgctcaggc tgtgatatcc    900
aatatggagt ttgtccagtt ccatccaact gcactatcag acgaaggcct cccaataaag    960
ccagctaaaa caagagataa tgcatttctc gtaacagaag cagtcagagg agatggagga    1020
attctttaca accaatccat ggagagattt atgcctttat acgacgaccg tgctgagttg    1080
gcaccaaggg atgtggttgc aagaagcata gatgatcaac tgaagaaacg tggagagaag    1140
```

-continued

```
tatgttctgt tggacatcag ccacaagcca agggaaaaaa ttcttgctca ttttcccaac    1200
attgcagctg aatgcctgct gcacggtctg gacatcacac agcaacccat acctgtcgtc    1260
cctgcagctc attacatgtg cggtggtgtt cgggctgggt tgcaaggga gacaagtgtg     1320 agaggcttgt atgtcgctgg tgaggttgct tgcactggat tgcacggtgc taatcgtctt    1380
gcaagcaact cattgctgga agcattggta ttcgctcaga gagccgtgca gccctctatc    1440
gaccacatgg tggatgctga tgctgacccg tgtctcgcag agaaatgggc acggcctgtg    1500
ctctctgtct ccattaggga cagtgcactg tctgacatca ttgagaggac aaagaagacc    1560
aggatggagc tacaatccat aatgtgggag tatgtcggta tagtgcggtc aacgaaccgg    1620
ctaaagaatg cagaatggaa gattggtgat ctagagtcag agtgggagga attcttattc    1680
agggggggct ggaagcctgc cacggtgggg atcgaggcct gcgaaatgag gaacctcttc    1740
tgctgcgcaa agctggttgt gaagagcgcg cttgcgaggc gggagagccg tggcctgcac    1800
ttcacagagg acttccctta cctggaggag agcaagagga agcctacagt gatcttccct    1860
actgctatcc aagagctgac atggagttca aagccattgc agaggcagct gcagtgcaaa    1920
tag                                                                   1923
```

<210> SEQ ID NO 17
<211> LENGTH: 32
<212> TYPE: DNA
<213> ORGANISM: Artificial Sequence
<220> FEATURE:
<223> OTHER INFORMATION: Synthetic primer

<400> SEQUENCE: 17
gagagacccg ggatggcggc tcatgtttct ac                                   32

<210> SEQ ID NO 18
<211> LENGTH: 34
<212> TYPE: DNA
<213> ORGANISM: Artificial Sequence
<220> FEATURE:
<223> OTHER INFORMATION: Synthetic primer

<400> SEQUENCE: 18
gagagacagc tgaatcgtta gttattcact cgac                                 34

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
gatcgttcac cgtgctgata                                                 20

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
tgtgttcaag ccatcctgag                                                 20

PLANTS WITH INCREASED YIELD AND METHOD FOR PRODUCING SAID PLANTS

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "2017-08-08 Sequence Listing 3493-0582PUS1.txt" created on Aug. 4, 2017 and is 47,266 bytes in size. The sequence listing contained in this .txt file is part of the specification and is hereby incorporated by reference herein in its entirety.

The present invention relates to a method for increasing the biomass of a plant, in particular a method for increasing the growth of a plant, more particularly for increasing the growth rate of a plant, for increasing the seed yield, for increasing the abiotic stress resistance, the biotic stress resistance and for increasing the germination rate, and the plants which result therefrom, by means of increasing the expression of L-aspartate oxidase in the plant. The method according to the invention enables an increase in the photosynthetic capacities of the plants via an increase in the amounts of NAD and derivatives thereof in said plants.

The development of sustainable agriculture faces a major challenge for the international community in coming years which consists in maintaining growth in food production at the same rate as that of the world population which is unfortunately accompanied by a worldwide decrease in high-quality arable land. Accepting this challenge will require efforts in several fields, one of which will be to provide crops of increased nutritional value able to resist various environmental stresses, to provide greater yield with fewer inputs and to grow faster, in order ultimately to deliver a better crop yield and an increased biomass.

Food safety has always been a priority throughout the world and an increasing concern in terms of the environmental impact of agricultural production which requires the development and use of new methods for improving productivity while protecting the environment. There is a greater need for better approaches for improving crop yields under various soil conditions.

In order to increase the yields and available biomass of crop plants, efforts have been made to modify the lignin content of plants. Other means for increasing biomass have been studied, such as plant genetic engineering, such as, for example, genetic manipulation of plant growth regulators or of photosynthetic pathways.

WO 2012/041496 describes a selection method using a PCR technique targeting a group of marker genes of energy use efficiency in order to produce plants having better vigor and better abiotic stress tolerance.

US 2006100573 describes a method which consists in overproducing a secondary metabolism enzyme (C3'H) involved in lignin synthesis in order to produce more wall and thus more biomass and more seeds.

US 20060095981 describes a method which consists in producing transgenic plants containing the glycolate-utilizing pathways from bacteria in order to reduce yield losses associated with photorespiration. Unfortunately, these plants produce active forms of oxygen which stress the plants produced (Kebeish et al., 2007; Maier et al., 2012).

However, each of these methods is directed at a particular metabolic pathway that does not address problems of biomass production, abiotic stress resistance, biotic stress resistance, germination regulation, seed yield, in a comprehensive manner.

There is also a method for treating seeds with an insecticidal molecule of the neonicotinoid family in order to increase yields (WO 01/26468). However, the use of these molecules, structurally similar to pyridine nucleotides such as nicotinic acid and its precursor, $NAD^+$, is controversial due to their impact on bee mortality.

U.S. Pat. No. 6,271,031 describes polynucleotides encoding polypeptides and, among others, L-aspartate oxidase. The object of the invention described in U.S. Pat. No. 6,271,031, however, is directed at modifying quinolinate production and does not teach any relationship to a phenotype linked to the growth of the plant thus transformed. The object of the invention describes the production of cDNA encoding L-aspartate oxidase but no example describes the effects of its use in plants.

US2007/016976 describes several thousand polynucleotide sequences the expression of which is altered, either toward overexpression or toward underexpression, in response to infection by a pathogen. One sequence among them corresponds to L-aspartate oxidase but nothing is disclosed as to a phenotypic effect on the growth of a modified plant. Moreover, no example of a plant whose expression of L-aspartate oxidase is disclosed. The fact that the expression of thousands of genes either induced or repressed by metabolic alteration as a result of a disease in no way proves the involvement of each of the deregulated genes in potential resistance to diseases.

WO9904012 describes methods used to increase plant resistance to pathogens by expression of an enzyme producing a hydrogen peroxide/reactive oxygen species or an oxalate degrading enzyme. This document mentions about 25 enzymes, among which L-aspartate oxidase, capable of producing a reactive oxygen species. However, it is disputed that L-aspartate oxidase can produce a reactive oxygen species and, furthermore, no example of WO9904012 describes such production. Indeed, unlike the bacterial isoform of the enzyme, plant L-aspartate oxidase does not appear capable of producing oxygen peroxide in the presence of molecular oxygen, but its activity would be that of a succinate dehydrogenase. Moreover, it is well-known that in plants, it is the NADPH oxidases which are the main sources of production of active forms of oxygen in response to pathogen attack.

WO2010086220 describes a method for increasing the yield of plants by modification of nitrogen metabolism via genetic transformation, producing greener plants via higher chlorophyll production. With regard to modification of L-aspartate oxidase expression, no example shows the effect of L-aspartate oxidase overexpression on plant phenotype. Also, no effect on yield or growth rate of these plants is mentioned.

The Inventors of the present invention have now discovered, surprisingly, that overexpression of the L-aspartate oxidase enzyme (first enzyme of the $NAD^+$ biosynthesis pathway) of a plant leads to a considerable increase in the photosynthetic capacities of the plant, which results in an acceleration of growth, an increase in biomass produced, an increase in yield, in particular in seed yield. Also observed is an acceleration of germination, an increase in abiotic stress resistance and an increase in biotic stress resistance in plants overexpressing L-aspartate oxidase.

Overexpression of L-aspartate oxidase, the first enzyme of the so-called de novo biosynthesis pathway of NAD (Noctor et al., 2006), results in an increase in the levels of NAD and derivatives thereof produced by plants. The result is a substantial increase in NAD content (NAD pool representing $NAD^+$, NADH, $NADP^+$ and NADPH) and in all pyridine nucleotides in plants overexpressing L-aspartate oxidase, but also in the level of other energy metabolites such as ATP. High energy content plants, plant cells or plant parts are thus produced.

Remarkable physiological consequences such as increased photosynthetic capacities and growth rates are thus observed in plants overexpressing L-aspartate oxidase. The result is a significant increase in biomass, but also in seed yield, when plants overexpressing L-aspartate oxidase are cultivated to maturity. These increased yields are strongly correlated with levels of overproduction of L-aspartate oxidase and NAD.

A very large increase in plant resistance to environmental abiotic stress conditions, such as a combination of intense heat and/or intense light, is observed in plants overexpressing L-aspartate oxidase.

This observation makes it possible to envisage reducing phytosanitary interventions on crop plants overproducing L-aspartate oxidase and also extending cultivation of a species overproducing L-aspartate oxidase beyond the geographic region usually reserved for cultivated species not overexpressing L-aspartate oxidase.

A significant increase in plant resistance to environmental biotic stress conditions, such as aphid attack, is observed in plants overexpressing L-aspartate oxidase.

This observation makes it possible to envisage decreasing phytosanitary treatments, in particular insecticides, on crop plants overproducing L-aspartate oxidase, particularly when environmental conditions are favorable to multiplication of pathogens or pests.

Seeds of plants overexpressing L-aspartate oxidase germinate faster and more homogeneously than those of plants not overexpressing L-aspartate oxidase. This can enable crop plants overproducing L-aspartate oxidase to become established faster, limiting competition from adventive species and yield losses. Also for this reason, crop plants overexpressing L-aspartate oxidase will have less need for herbicidal treatments targeting crop weeds.

Under unfavorable environmental conditions such as nitrogen-deficiency, seeds of plants overexpressing L-aspartate oxidase germinate faster and, very important, maintain a maximum germination capacity under these conditions, whereas the germination capacity of plants not overexpressing L-aspartate oxidase is much lower. The present invention makes it possible to envisage decreasing the supply of nitrogen inputs for crops overexpressing L-aspartate oxidase.

Overexpression of L-aspartate oxidase in plants according to the invention makes it possible to avoid a seed priming treatment, in particular in edible species, a financially expensive methodology usually used to break the dormancy, to accelerate and to homogenize the germination of commercial seeds.

The present invention thus relates to a method for improving at least one phenotypic trait selected from biomass, yield, in particular seed yield, abiotic stress resistance, biotic stress resistance, germination rate or growth rate, of a plant, said method comprising overexpression of L-aspartate oxidase.

In a particular embodiment, the method according to the present invention comprises transformation of a plant cell with at least one nucleic acid that encodes L-aspartate oxidase, and generation from such a cell of a plant that overexpresses L-aspartate oxidase.

In a particular embodiment, the method according to the invention is a method for improving yield, in particular seed yield, of a plant, which method comprises transformation of a plant cell with at least one nucleic acid that encodes L-aspartate oxidase, thus generating a plant that overexpresses L-aspartate oxidase, and cultivation of the plant to maturity.

In a particular embodiment, the method according to the invention is a method for improving the germination rate of a plant, which method comprises transformation of a plant cell with at least one nucleic acid that encodes L-aspartate oxidase, thus generating a plant that overexpresses L-aspartate oxidase, and cultivation of the plant to maturity.

The present invention thus relates to a method for improving at least one phenotypic trait selected from biomass, yield, in particular seed yield, abiotic stress resistance, biotic stress resistance, germination rate or growth rate, of a plant, said method comprising overexpression of L-aspartate oxidase, which results in increased amounts of NAD and derivatives thereof.

In another embodiment, the method according to the present invention is directed at improving the biomass production of a plant, which method comprises transformation of a plant cell with at least one nucleic acid that encodes L-aspartate oxidase, thus generating a plant that overexpresses L-aspartate oxidase, and cultivation of the plant to maturity.

Plants according to the invention thus have increased amounts of NAD and derivatives thereof.

The methods according to the invention are also directed at increased amounts of NAD and derivatives thereof.

It is also an object of the present invention to provide a method for improving abiotic stress resistance and/or biotic stress resistance of a plant, which method comprises transformation of a plant cell with at least one nucleic acid that encodes L-aspartate oxidase, thus generating a plant that overexpresses L-aspartate oxidase, and cultivation of the plant to maturity.

In a method according to the present invention, the at least one nucleic acid that encodes L-aspartate oxidase is under the control of a promoter ensuring overexpression of L-aspartate oxidase.

In another preferred embodiment of the present invention, the at least one nucleic acid comprises a nucleic acid selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16.

In an embodiment of the method according to the invention, the at least one nucleic acid comprises a nucleic acid according to SEQ ID NO: 1.

A method according to the present invention is also directed at a method in which the plant is selected from the group consisting of wheat, barley, rice, maize, sorghum, sunflower, rapeseed, soybean, cotton, pea, common bean, cassava, mango, banana, potato, tomato, pepper, melon, zucchini, watermelon, lettuce, cabbage, eggplant, poplar.

In a particular embodiment of the method according to the present invention, the plant is rice (*Oryza sativa*), wheat, barley or maize.

In an embodiment of the present invention, overexpression of L-aspartate oxidase is achieved by introgression of a genetic element encoding overexpression of L-aspartate oxidase.

Plants according to the invention thus have increased amounts of NAD and derivatives thereof.

The methods according to the invention are also directed at increased amounts of NAD and derivatives thereof.

It is thus an object of the present invention to provide a method in which introgression of a genetic element encoding overexpression of L-aspartate oxidase is produced by protoplast fusion.

It is also an object of the present invention to provide a method in which introgression of a genetic element encoding overexpression of L-aspartate oxidase is produced by embryo rescue.

The present invention also relates to a method for producing a plant exhibiting at least one improved phenotypic trait selected from biomass, germination rate, yield, in particular seed yield, abiotic stress resistance, biotic stress resistance, germination rate, growth, method comprising detection of the presence of a genetic element, in particular a nucleic acid sequence, linked to overexpression of L-aspartate oxidase in a donor plant, and transfer of the genetic element, in particular a nucleic acid sequence, linked to overexpression of the L-aspartate oxidase thus detected, from the donor plant to a recipient plant.

Overexpression of L-aspartate oxidase results in increased amounts of NAD and derivatives thereof.

In a particular embodiment of a method according to the invention, detection is carried out using at least one molecular marker.

In an alternative embodiment of a method according to the invention, detection is carried out by measuring L-aspartate oxidase enzymatic activity in the donor plant.

The present invention also relates to a method for increasing at least one phenotypic trait selected from biomass, germination rate, yield, in particular seed yield, abiotic stress resistance, biotic stress resistance, germination rate, growth, of a plant, comprising provision of a plant population and selection of individuals of the population that exhibit the highest L-aspartate oxidase expression possible.

In a particular embodiment of the invention, the plant population is a population of mutant plants.

Particularly, the population of mutant plants is produced by TILLING.

It is also an object of the present invention to provide a method which comprises selection, within a plant population, of at least one plant exhibiting overexpression of L-aspartate oxidase in relation to the L-aspartate oxidase expression of the parent plants.

In a particular embodiment of the present invention, introgression comprises:
 a) Providing a plant having a given level of L-aspartate oxidase expression,
 b) Providing a plant having an increased level of L-aspartate oxidase expression in relation to the plant provided in a),
 c) Crossing the plant provided in a) with the plant provided in b),
 d) Generating progeny resulting from the crossing c),
 e) Selecting among the progeny at least one plant having a higher level of expression of L-aspartate oxidase than that of the plant provided in b).

In a particular embodiment, the method described above comprises an additional step of crossing the plant selected in e) with the plant provided in b) followed by an additional step of selecting among the progeny produced at least one plant having a higher level of expression of L-aspartate oxidase than that of the plant selected in e).

It is also an object of the present invention to provide a method for selecting a plant, characterized in that it comprises searching for an allele of the L-aspartate oxidase enzyme gene having a mutation resulting in an improvement in at least one phenotypic trait selected from biomass, seed yield, abiotic stress resistance, biotic stress resistance, growth rate or germination rate.

The present invention also relates to a plant able to be produced by a method according to one of the embodiments described herein.

Lastly, the present invention also relates to the use of a plant produced by a method according to one of the embodiments described herein, or a derivative of such a plant, for the preparation of a composition intended for human consumption, for animal feed or for the preparation of biofuels.

An object of the present invention is thus the use of at least one nucleic acid that encodes L-aspartate oxidase, and the encoded L-aspartate oxidase protein, for producing a plant that exhibits at least one phenotypic trait selected from increased biomass, increased germination rate, increased growth rate, increased yield, in particular increased seed yield, increased abiotic stress resistance, increased biotic stress resistance, increased germination rate, accelerated growth, via overexpression of L-aspartate oxidase.

The invention provides a method for producing at least one phenotypic trait selected from increased biomass, increased germination rate, increased yield, in particular increased seed yield, increased abiotic stress resistance, increased biotic stress resistance, increased germination rate, accelerated growth, of a plant, comprising the step consisting in overexpressing L-aspartate oxidase in the cells of said plant.

Overexpression of L-aspartate oxidase in the cells of the plant can be produced by various means at the disposal of the skilled person, whether by transgenesis, by transformation, by introgression, by selection, by marker-assisted selection, by random or directed mutagenesis followed by selection or not, for example.

Overexpression of L-aspartate oxidase results in increased amounts of NAD and derivatives thereof.

A particular object of the invention is a method for producing a plant or a plant part exhibiting at least one phenotypic trait selected from increased biomass, increased germination rate, increased yield, in particular increased seed yield, increased abiotic stress resistance, increased biotic stress resistance, increased germination rate, accelerated growth, which method comprises transformation of a plant cell with at least one nucleic acid that encodes L-aspartate oxidase, and generation from such a cell of a plant that overexpresses L-aspartate oxidase.

The method according to the invention for improving at least one phenotypic trait selected from biomass, yield, in particular seed yield, abiotic stress resistance, biotic stress resistance, germination rate or growth of a plant, comprises transformation of a plant cell with at least one nucleic acid that encodes L-aspartate oxidase, and generation from such a cell of a plant that overexpresses L-aspartate oxidase.

In a particular embodiment, the at least one nucleic acid that encodes L-aspartate oxidase is under the control of a promoter ensuring overexpression of L-aspartate oxidase.

Another object of the invention is method for producing a plant cell, a plant or a plant part exhibiting at least one phenotypic trait selected from increased biomass, increased germination rate, increased yield, in particular increased seed yield, increased abiotic stress resistance, increased biotic stress resistance, increased germination rate, accelerated growth, which method comprises the step consisting in transforming a plant cell with at least one nucleic acid that encodes L-aspartate oxidase, and can comprise the additional step of generating therefrom a plant that overexpresses L-aspartate oxidase.

The present invention relates to a method for producing plants enriched in pyridine nucleotides, having increased biomass and seed yield and exhibiting strong resistance to environmental stresses. The targeted increase in NAD content via overexpression of L-aspartate oxidase in the cells of the plant leads to an increase in energy metabolite content. This strategy of overexpression of a gene sequence represents a novel genetic improvement that enables the plants to exceed their maximum yield potential.

The methods according to the present invention provide the following advantages:
- constitutively increasing the biomass of the plants throughout their development, and thus increasing the crop yield;
- significantly increasing the seed yield of the plants;
- increasing earlier production of biomass and seed and earlier germination;
- enabling the production of plants resistant to conditions of intense heat and light, which limits yield losses under these conditions;
- enabling plants to better resist various biotic stresses such as attacks by pests such as aphids, which makes it possible to envisage decreased phytosanitary treatments of crops, insecticides in particular;
- enabling plants to increase their germination rate, thus the establishment of a crop;
- enabling plants to break dormancy more easily (particularly true in certain plant species that require priming in order to germinate);
- enabling plants to maintain a strong germination capacity, particularly in a nitrogen-poor environment, which makes it possible to envisage a limited provision of nitrogen to these crops, therefore limiting costs and agricultural pollution;
- and enabling the production of plants with the best energy status, which makes it possible to envisage decreased phytosanitary crop treatments.

Moreover, the method developed for measuring L-aspartate oxidase activity in plant tissues can be used as a biochemical marker of energy homeostasis state for improving plants but also as selection marker for plants according to the invention overexpressing L-aspartate oxidase.

Plant parts can be roots, leaves, trunk, stem, fruits, storage organs and flowers, for example.

The invention further proposes a method for improving yield, in particular seed yield, of a plant, which method comprises transformation of a plant cell with at least one nucleic acid that encodes L-aspartate oxidase, thus generating a plant that overexpresses L-aspartate oxidase, and cultivation of the plant to maturity.

The invention further proposes a method for improving biomass production of a plant, which method comprises transformation of a plant cell with at least one nucleic acid that encodes L-aspartate oxidase, thus generating a plant that overexpresses L-aspartate oxidase, and cultivation of the plant to maturity.

The invention further proposes a method for improving abiotic stress resistance of a plant, which method comprises transformation of a plant cell with at least one nucleic acid that encodes L-aspartate oxidase, thus generating a plant that overexpresses L-aspartate oxidase, and cultivation of the plant to maturity.

The invention further proposes a method for improving biotic stress resistance of a plant, which method comprises transformation of a plant cell with at least one nucleic acid that encodes L-aspartate oxidase, thus generating a plant that overexpresses L-aspartate oxidase, and cultivation of the plant to maturity.

In a particular embodiment of the present invention, the transformation of a plant cell comprises transformation with at least one nucleic acid that encodes L-aspartate oxidase. Thus in such cases, transformation comprises transformation with a nucleic acid encoding L-aspartate oxidase in multiple copies, which enables the production of the protein in increased amounts, and thus overexpression of this enzyme. Transformation can be carried out with two copies of a nucleic acid encoding L-aspartate oxidase, particularly with three copies of a nucleic acid encoding L-aspartate oxidase, more particularly with four copies of a nucleic acid encoding L-aspartate oxidase, even more particularly with five copies, or more, of the nucleic acid encoding L-aspartate oxidase.

In a particular embodiment of a method according to the invention, the nucleic acid that encodes L-aspartate oxidase is under the control of a promoter ensuring overexpression of L-aspartate oxidase.

Another object of the invention is a plant cell, a plant or a plant part, which is transgenic for at least one nucleic acid that encodes L-aspartate oxidase and which it overexpresses.

A nucleic acid encoding L-aspartate oxidase can be any nucleic acid encoding the functional enzyme in such a way that when introduced into a host cell and under the control of an appropriate promoter, the amount of L-aspartate oxidase and/or the enzymatic activity thereof within the cell is increased.

For example, a nucleic acid encoding L-aspartate oxidase can be the nucleic acid having the sequence SEQ ID NO: 1 corresponding to *Arabidopsis thaliana*.

This sequence SEQ ID NO: 1 corresponds, strictly speaking, to a nucleic acid encoding *Arabidopsis thaliana* L-aspartate oxidase and comprises a portion encoding a plastid-targeting peptide.

More particularly, in the context of the present invention, the nucleic acid encoding L-aspartate oxidase:
i) has a sequence having at least 55% homology with SEQ ID NO: 1 or the complementary sequence thereof, or
ii) has a sequence that hybridizes to SEQ ID NO: 1 or the complementary sequence thereof, under stringency conditions, and which encodes L-aspartate oxidase.

In a particular embodiment, the nucleic acid encoding L-aspartate oxidase has a sequence having at least 60%, at least 65%, at least 70%, at least 75%, at least 80%, at least 85%, at least 90%, at least 92%, at least 93%, at least 94%, at least 95%, at least 96%, at least 97%, at least 98%, at least 99% homology with SEQ ID NO: 1.

The nucleic acid encoding L-aspartate oxidase to be transferred in order to overexpress L-aspartate oxidase can also be a nucleic acid homologous to the host plant selected from the nucleic acids of plants, microorganisms or algae.

In the context of implementation of microorganism nucleic acids encoding L-aspartate oxidase, it will be advisable to prepare a construction by ligation with a sequence encoding a targeting peptide such as, for example, a plastid-targeting peptide, such as that of the RuBisCO small subunit.

The term "homologous" or "homology" refers to any nucleic acid or protein having one or more sequence modification(s) in relation to all or part of the sequence SEQ ID NO: 1 or of the sequence SEQ ID NO: 2, respectively, while retaining most or all of the L-aspartate oxidase activity.

In an embodiment of the present invention, overexpression of L-aspartate oxidase in plants can be produced using nucleic acids or proteins comprising any one of the following nucleotide or amino acid sequences: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16.

In a particular embodiment of the present invention, the nucleic acid encoding L-aspartate oxidase comprises a nucleic acid selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16.

In a particular embodiment, the nucleic acid encoding L-aspartate oxidase has a sequence having at least 60%, at least 65%, at least 70%, at least 75%, at least 80%, at least 85%, at least 90%, at least 92%, at least 93%, at least 94%, at least 95%, at least 96%, at least 97%, at least 98%, at least 99% homology with the nucleic acid sequence selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16.

The present invention further proposes an expression cassette comprising a promoter expressible in a plant functionally linked to a coding region containing at least one nucleic acid encoding an L-aspartate oxidase, in which said promoter is not an L-aspartate oxidase promoter. Said promoter can be a 35S promoter, a ubiquitin promoter or an actin promoter, for example.

The term "transgenic" means that the plant cell or the plant comprises in its genome at least one nucleic acid encoding L-aspartate oxidase that is foreign to this plant or plant cell, or that comprises in its genome at least one endogenous coding sequence of L-aspartate oxidase functionally linked to at least one regulatory region, for example a promoter, that is not present in the endogenous gene of this plant or plant cell. In general, the foreign nucleic acid is integrated stably in the genome so that the polynucleotide is transmitted to successive generations. The term "transgenic" also includes the case in which the plant cell or the plant comprises in its genome two or more than two nucleic acids, endogenous or exogenous to the cell or plant species, encoding L-aspartate oxidase, thus enabling overexpression of L-aspartate-oxidase. The term "overexpression" herein is intended to mean both an increase in the amount of L-aspartate oxidase in relation to the amount expressed in a control plant, and ectopic expression of this enzyme, in a tissue or a compartment and/or at a developmental stage where it is not normally expressed. It includes the situation in which the L-aspartate oxidase is endogenous or heterologous, i.e. when it is from an organism, such as a plant, different from the host cell, or in which at least one transcriptional regulatory region of L-aspartate oxidase is not present in the endogenous gene. The amount and/or the activity of the L-aspartate oxidase protein expressed in a plant cell can be determined in nmol of iminoaspartate produced per minute per milligram of protein or in nmol of iminoaspartate produced per minute per milligram of chlorophyll, by measuring the $NH_4^+$ released by the quasi-instantaneous decomposition of iminoaspartate under the test measurement conditions.

The term "overexpression" also means that the enzymatic activity of the L-aspartate oxidase produced in the host cell after introduction of the sequence encoding L-aspartate oxidase, for equal amounts of enzyme produced, is higher than the enzymatic activity of the L-aspartate oxidase of the host cell before the introduction of said sequence. Such specific overactivity can be due to a difference in the primary, secondary or tertiary structure of the protein due to a difference in the nucleic acid sequence encoding same.

Overexpression of L-aspartate oxidase results in increased amounts of NAD and derivatives thereof.

Plants according to the invention thus have increased amounts of NAD and derivatives thereof.

The methods according to the invention are also directed at increased amounts of NAD and derivatives thereof.

NAD (nicotinamide adenine dinucleotide) is an oxidation-reduction coenzyme present in all living cells. The compound is a dinucleotide, since it consists of two nucleotides joined through their phosphate groups. One nucleotide contains an adenine while the other contains a nicotinamide. In metabolism, $NAD^+$ is involved in redox reactions as electron transporter. This coenzyme is present in two forms in the cell. $NAD^+$ is an oxidizing agent and NADH is a reducing agent.

The expression "NAD and derivatives thereof" means NAD, $NAD^+$, NADP, $NADP^+$ and NADPH.

Nicotinamide adenine dinucleotide phosphate (NADP) is an oxidation-reduction coenzyme. It is very similar to nicotinamide adenine dinucleotide (NAD), from which it differs by the presence of a phosphate group on the second carbon of the β-D-ribofuranose of the adenosine residue. Its reduced form is designated NADPH or $NADPH_2$ or $NADPH+H^+$.

An "increase" in at least one phenotypic trait selected from growth, size and/or weight, yield, in particular seed yield, growth rate, growth, germination rate, biomass, abiotic stress resistance, biotic stress resistance, observed in plants according to the invention that overexpress L-aspartate oxidase indicates that this at least one trait is quantitatively significantly higher than that of control plants of the same species which have not undergone transformation with a nucleic acid encoding L-aspartate oxidase, or which have not undergone introgression of a genetic element encoding said L-aspartate oxidase, when they are cultivated under the same growth conditions.

In the context of the invention, the expression "control plant" means a plant that has the same genetic background as a plant according to the present invention in which the control plant does not have the nucleic acid or the genetic element enabling overexpression of L-aspartate oxidase according to the present invention; overexpression linked to an increase in a phenotypic trait selected from increased biomass, increased germination rate, increased yield, in particular increased seed yield, increased abiotic stress resistance, increased biotic stress resistance, increased germination rate, accelerated growth. A control plant is cultivated for the same duration of time and under the same conditions as a plant according to the present invention.

The expression "variety," "cultivar" or "new variety of plant" is understood herein according to the definition of UPOV. Thus, a control plant can be a variety, a pure line or a hybrid, on the condition of having the same genetic background as the plant according to the present invention except for the nucleic acid, or the genetic element, enabling the improvement of at least one phenotypic trait selected from biomass, germination rate, yield, in particular seed yield, abiotic stress resistance, biotic stress resistance, germination rate, growth, according to the present invention and linked to overexpression of L-aspartate oxidase.

In the methods or plants of the invention, the nucleic acid or genetic element encoding L-aspartate oxidase can be heterologous in relation to the plant into which it is introduced or can belong to the same species insofar as it can be expressed in the plants in amounts greater than the amount conventionally produced by an untransformed plant or a plant that did not contain the sequence or element introduced or introgressed. Thus, any nucleotide sequence encoding L-aspartate oxidase can be used, for example a wild-type sequence for the L-aspartate oxidase gene, a sequence mutated at the encoding portion of the enzyme causing higher specific activity or a sequence mutated at the promoter region causing higher production of the protein and thus overexpression of the enzyme, or a combination of the two scenarios.

Advantageously, a nucleic acid encoding L-aspartate oxidase used to transform cells or plants according to the invention comprises a nucleic acid encoding the protein of SEQ ID NO: 2, for example the coding sequence of the *Arabidopsis thaliana* cDNA of SEQ ID NO: 1.

In a preferred embodiment of the method according to the invention, the plant is selected from the group consisting of wheat, barley, rice, maize, sorghum, sunflower, rapeseed, soybean, cotton, pea, common bean, cassava, mango, banana, potato, tomato, pepper, melon, zucchini, watermelon, lettuce, cabbage, eggplant, poplar.

In a preferred embodiment of the method according to the invention, the plant is selected from the group comprising wheat, barley, rice, maize.

In a more preferred embodiment of the method according to the invention, the plant is Asian rice (*Oryza sativa*) or African rice (*Oryza glaberrima*) or the hybrid rice of these two species.

An embodiment of the invention comprises overexpression of L-aspartate oxidase in a monocotyledon, in particular rice (*Oryza sativa*), by overexpression of L-aspartate oxidase encoded by a nucleic acid selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 in rice plant cells.

An embodiment of the invention comprises overexpression of L-aspartate oxidase in a monocotyledon, in particular rice (*Oryza glaberrima*), by overexpression of L-aspartate oxidase encoded by a nucleic acid selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 in rice plant cells.

An embodiment of the invention comprises overexpression of L-aspartate oxidase in a monocotyledon, in particular wheat (*Triticum*), by overexpression of L-aspartate oxidase encoded by a nucleic acid selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 in wheat plant cells.

An embodiment of the invention comprises overexpression of L-aspartate oxidase in a monocotyledon, in particular barley (*Hordeum vulgare*), by overexpression of L-aspartate oxidase encoded by a nucleic acid selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 in barley plant cells.

An embodiment of the invention comprises overexpression of L-aspartate oxidase in a monocotyledon, in particular maize (*Zea mays*), by overexpression of L-aspartate oxidase encoded by a nucleic acid selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 in maize plant cells.

An embodiment of the invention comprises overexpression of L-aspartate oxidase in a monocotyledon, in particular sorghum (*Sorghum bicolor*), by overexpression of L-aspartate oxidase encoded by a nucleic acid selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 in *sorghum* plant cells.

An embodiment of the invention comprises overexpression of L-aspartate oxidase in a dicotyledon, in particular cotton (*Gossypium hirsutum*) by overexpression of L-aspartate oxidase encoded by a nucleic acid selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 in cotton plant cells.

An embodiment of the invention comprises overexpression of L-aspartate oxidase in a dicotyledon, in particular tomato (*Solanum lycopersicum*), by overexpression of L-aspartate oxidase encoded by a nucleic acid selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 in tomato plant cells.

An embodiment of the invention comprises overexpression of L-aspartate oxidase in a dicotyledon, in particular rapeseed (*Brassica napus*), by overexpression of L-aspartate oxidase encoded by a nucleic acid selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 in rapeseed plant cells.

An embodiment of the invention comprises overexpression of L-aspartate oxidase in a dicotyledon, in particular soybean (*Glycine max*), by overexpression of L-aspartate oxidase encoded by a nucleic acid selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 in soybean plant cells.

An embodiment of the invention comprises overexpression of L-aspartate oxidase in a dicotyledon, in particular sunflower (*Helianthus annuus*), by overexpression of L-aspartate oxidase encoded by a nucleic acid selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 in sunflower plant cells.

An embodiment of the invention comprises overexpression of L-aspartate oxidase in a dicotyledon, in particular common bean (*Phaseolus vulgaris*), by overexpression of L-aspartate oxidase encoded by a nucleic acid selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 in common bean plant cells.

An embodiment of the invention comprises overexpression of L-aspartate oxidase in a dicotyledon, in particular poplar (*Populus trichocarpa*), by overexpression of L-aspartate oxidase encoded by a nucleic acid selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 in poplar plant cells.

The skilled person knows how to identify nucleic acid sequences encoding L-aspartate oxidase in various species, by comparing SEQ ID NO: 1 with sequences from other species, with a computer program such as BLAST (National Center for Biotechnology Information (NCBI)) and fast DB with the default settings. The skilled person could also use a nucleic acid sequence selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 in order to perform sequence comparisons to identify and find suitable sequences encoding L-aspartate oxidase.

These algorithms are described in "Current methods of sequencing and synthesis methods and applications", pages 127-149, 1988, in Alabama R. Liss, Inc.

Homologous sequences are preferably defined as follows:
i) DNA sequences which show similarity or identity of at least 55%, preferably at least 70%, preferably at least 80%, more preferably at least 90%, more preferably still at least 95% with the sequence SEQ ID NO: 1; or with a sequence selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16,
ii) sequences which hybridize with the sequence of SEQ ID NO: 1, or with a sequence selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 or with the complementary sequence thereof, under hybridization stringency conditions, for example low stringency, or
iii) sequences encoding an L-aspartate oxidase enzyme comprising the amino acid sequence of SEQ ID NO: 2, or a homologous amino acid sequence, for example any amino acid sequence with L-aspartate oxidase enzymatic activity and having at least 60%, preferably at least 70%, preferably at least 80%, even more preferably at least 90%, more preferably still at least 95% sequence identity with the sequence of SEQ ID NO: 2.

Preferably, such a homologous nucleotide sequence hybridizes specifically to sequences complementary to the sequence SEQ ID NO: 1 or to a sequence selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, under rigorous conditions. The parameters which define the stringency conditions depend on the temperature (Tm) at which 50% of the paired strands separate.

Low-stringency hybridization conditions are those in which hybridization is observed using a hybridization temperature 5 to 10° C. below Tm, and the hybridization buffers are high ionic strength solutions, for example 6×SSC solution.

The terms "sequence similarity" or "sequence identity" or "sequence homology" are used herein interchangeably and mean in the context of two or more nucleic acid or protein sequences that are the same or have a specified percentage of amino acid or nucleotide residues that are the same, when compared and aligned for maximum correspondence, as measured using one of the following sequence comparison algorithms or by visual inspection, if two sequences to be compared have different lengths, sequence identity preferably relates to the percentage of nucleotide residues of the shortest sequence that are identical to the nucleotide residues of the longer sequence. Sequence identity can be determined conventionally using computer programs such as BestFit (Wisconsin Sequence Analysis Package, Version 8 for Unix, Genetics Computer Group, University Research Park, 575 Sciences Drive, Madison, Wis. 53711). BestFit uses the local homology algorithm of Smith and Waterman (1981) to find the segment having the highest sequence identity between the two sequences. When BestFit or any other sequence alignment program is used to determine if a particular sequence is present, for example 95% identity with a reference sequence of the present invention, the parameters are preferably adapted so that the percent identity is calculated over the entire length of the reference sequence and that variations in homology of up to 5% of the total number of nucleotides in the reference sequence are allowed.

A nucleic acid is homologous to a sequence, such as the sequence (coding sequence, CDS) represented in SEQ ID NO: 1 for example, as used herein, when it comprises a nucleotide sequence that differs from this sequence, for example SEQ ID NO: 1, by a mutation, insertion, deletion or substitution of one or more bases, or by degeneration of the genetic code, insofar as it encodes a polypeptide having the activity of the L-aspartate oxidase enzyme. A protein is homologous to the L-aspartate oxidase represented in SEQ ID NO: 2 when it comprises an amino acid sequence that differs from the sequence SEQ ID NO: 2 by mutation, insertion, deletion or substitution of one or more amino acids, provided it is a polypeptide having the activity of the L-aspartate oxidase enzyme.

L-aspartate oxidase (EC 1.4.3.16) is an enzyme that catalyzes the chemical reaction:

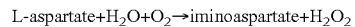

L-aspartate+$H_2O$+$O_2$→iminoaspartate+$H_2O_2$

The three substrates of this enzyme are L-aspartate, $H_2O$ and $O_2$, while its two products are iminoaspartate and $H_2O_2$. In solution at pH 8, the iminoaspartate produced during the enzymatic reaction, also called iminosuccinate, is unstable and produces $NH_4^+$ (half-life: 2.5 min).

L-aspartate oxidase is an enzyme that catalyzes the first step of de novo biosynthesis of $NAD^+$. Oxygen can be replaced by fumarate as electron acceptor, to give succinate. The ability of the enzyme to use both oxygen and fumarate as reoxidation cofactor enables it to function under aerobic and anaerobic conditions. The enzyme is a member of the succinate dehydrogenase/fumarate reductase enzyme family.

The expression "activity of the L-aspartate oxidase enzyme" or "L-aspartate oxidase enzymatic activity", as used herein, refers in particular to its oxidoreductase activity in plants, which can be determined by incubation of the protein with L-aspartate, fumarate and FAD for 30 minutes, followed by spectrophotometric measurement at OD 635 nm of $NH_4^+$ released by decomposition of iminoaspartate produced during the reaction. A detailed measurement protocol is described in the experimental section below.

The nucleic acid that encodes L-aspartate oxidase is generally inserted, in one or multiple copies, into a nucleotide construction, called an expression cassette, in which it is functionally linked to elements enabling its expression, more particularly its overexpression and optionally its regulation.

Among these elements, particular mention may be made of transcription promoters, activators and/or terminators.

In a particular embodiment, the plant cell is transformed with an expression cassette comprising at least one nucleotide sequence encoding L-aspartate oxidase and a promoter specific to a tissue. Expression in tissues containing lignin or in inflorescences can be of particular interest, as well as selective or preferential expression in flowers or seeds. A promoter specific to the root can also be useful. Expression in root tissues can be accomplished using the acidic chitinase gene (Samac et al., 1990) or the lower specific subdomains of the CaMV 35S promoter which have been identified (Benfield et al., 1989).

Among the transcription promoters which can be employed, mention may be made of: a 35S promoter, or the double constitutive 35S promoter (pd35S) of the cauliflower mosaic virus (CaMV), as described in Kay et al., 1987; a promoter PCRU of radish cruciferin which directs expression of the associated sequences only in the seeds of the transgenic plant; the promoters PGEA1 and PGEA6 which correspond to the 5' noncoding region of the seed storage protein genes (GEA1 and GEA6, respectively) of *Arabidopsis thaliana* which direct specific expression in seeds; the chimeric promoter PSP (Ni et al., 1995) which is a fusion of a triple repeat of an element activating transcription of the octopine synthase gene promoter in *Agrobacterium tumefaciens*; a rice actin promoter, optionally followed by the rice actin intron (RAP-RAI), for example; the promoter contained in the plasmid pAct1-F4 (Mc Elroy et al., 1991); the maize high-molecular-weight glutenin (HMWG) promoter; the maize zein gene promoter (P-zein) contained in the plasmid p63, which directs expression in seed albumen.

Other suitable promoters expressible in a plant in accordance with the present invention comprise, but are not limited to: promoters from the ubiquitin family (for example, the maize ubiquitin promoter of document EP 0 342 926), a rice actin promoter such as the promoter described by Mc Elroy et al., (already mentioned above) or the promoter described in U.S. Pat. No. 5,641,876; any one of the cassava vein mosaic virus promoters (WO 97/48819), any one of the series of subterranean clover stunt virus pPLEX promoters (WO 96/06932), or an alcohol dehydrogenase promoter, for example, pADH 1S (GenBank accession numbers X04049, X00581).

Among the terminators usable in the constructions of the invention, particular mention may be made of the 3' end of the *Agrobacterium tumefaciens* nopaline synthase gene.

The expression cassette can be inserted into a nucleotide vector, such as a plasmid, which can further comprise a marker gene, for example a gene for selecting a plant transformed from a plant that does not contain the transfected foreign DNA. A marker gene can in particular consist of a gene that confers resistance to an antibiotic or resistance to an herbicide, or resistance to an amino acid, for example.

The vector thus constructed can be used to transform host cells, according to techniques known to the skilled person.

Particular mention may be made of methods of direct transfer of genes in plant cells, such as transformation by *Agrobacterium tumefaciens*, direct microinjection in plant embryoids (Neuhaus et al., 1987), vacuum infiltration (Bechtold et al., 1993) or electroporation (Chupeau et al., 1989), or alternatively, direct precipitation using PEG (Schocher et al., 1986) or bombardment with particles coated with the plasmid DNA of interest, using a gun (Fromm M. et al., 1990), for example.

According to another embodiment of the method of the invention, plant cells are transformed with a vector as defined above, transferred into a cellular host able to infect said plant cells by enabling the integration, in the genome of the latter, of nucleotide sequences of interest initially contained in the genome of the above-mentioned vector. Advantageously, the cellular host used is a bacterial strain, such as *Agrobacterium tumefaciens* or *Agrobacterium rhizogenes*, for example.

To transform monocotyledons such as rice (*Oryza sativa*), the process described by Ishida et al. (1996) can be used or any one of the methods described in Hiei et al. (1994), Hiei et al. (1997), in U.S. Pat. No. 5,641,664 or 5,679,558, or in Christou et al. (1991). According to another protocol, transformation can be carried out according to the method described by Finer et al. (1992) using a particle gun with gold or tungsten particles, for example.

The plants thus produced overexpress L-aspartate oxidase.

Such plants or plant parts are advantageously produced by the method described above, in which a plant cell is transformed with at least one nucleic acid that encodes the L-aspartate oxidase enzyme, and cultured, yielding a plant that overexpresses L-aspartate oxidase.

Examples of transgenic plants include wheat, barley, rice, maize, *sorghum*, sunflower, rapeseed, soybean, cotton, pea, common bean, cassava, mango, banana, potato, tomato, pepper, melon, zucchini, watermelon, lettuce, cabbage, eggplant, poplar.

The increase in the growth of the plants, in particular of the roots, promotes the plants' vigor and their capacity to draw nutrient substrates and water from the soil or culture medium.

The growth rate and the increase in the growth rate of the plants, in particular of the inflorescences and the fruits, are advantageous for the production of seeds, fodder, flowers or fruits, in particular legume-fruits for horticultural crops.

Transgenic plants according to the invention include both first-generation plants and progeny thereof containing the expression cassette enabling overexpression of L-aspartate oxidase according to the invention (line varieties or hybrid varieties, in particular).

Plant parts comprise any tissue or organ, such as roots, flowers, stems, trunk, leaves, fruits, storage organs or seeds.

The present invention comprises in particular seeds that have increased expression of L-aspartate oxidase, produced by specific overexpression of an L-aspartate oxidase coding sequence in the seed.

In an embodiment of the invention, the expression cassette of the invention is used to overexpress L-aspartate oxidase in a plant or a plant cell. This use leads to increased biomass, plant growth, size, weight, yield and/or growth rate.

In another embodiment of the invention, the expression cassette according to the invention is used to increase at least one phenotypic trait selected from biomass, germination rate, yield, in particular seed yield, abiotic stress resistance, biotic stress resistance, germination rate, growth, of a plant cell, a plant or a plant part.

As mentioned above, the nucleic acid encoding overexpression of L-aspartate oxidase in plants according to the invention can be a member of the same species insofar as it can be expressed in the plants in higher amounts than the amount conventionally produced by a plant that did not contain the introduced nucleotide sequence or genetic element. Thus, any nucleotide sequence encoding L-aspartate oxidase can be used, for example a wild-type sequence for the L-aspartate oxidase gene, a mutated sequence of a wild-type sequence that encodes L-aspartate oxidase, or a mutated sequence of the gene promoter of a wild-type or mutated L-aspartate oxidase that induces an increase in the amount of L-aspartate oxidase or the stability of L-aspartate oxidase messenger RNA, or expression of an L-aspartate oxidase having higher enzymatic activity in relation to the amount and/or the activity of L-aspartate oxidase produced or expressed in the host plant before receiving the introduced sequence.

As indicated above, overexpression of L-aspartate oxidase in plant cells can be produced by various means at the disposal of the skilled person, whether by transgenesis, by transformation, by introgression, by selection, by marker-assisted selection, by random or directed mutagenesis followed by selection or not, for example.

In a particular embodiment of the method according to the present invention, overexpression of L-aspartate oxidase is achieved by introgression of a genetic element encoding overexpression of L-aspartate oxidase.

The expression "genetic element" or "genetic material" used herein refers to any gene, group of genes, QTL, locus, allele, chromosomal fragment, nucleotide sequence, nucleic sequence that is able to contribute to the increase in at least one phenotypic trait of the plant, selected from increased biomass, increased germination rate, increased yield, in particular increased seed yield, increased abiotic stress resistance, increased biotic stress resistance, increased germination rate, accelerated growth, by influencing the expression of L-aspartate oxidase on the level of the DNA itself, in terms of the level of translation, transcription and/or activation of a final polypeptide product, i.e., to regulate the metabolism of the plant leading to the phenotypic expression of the genotype.

In the context of the present invention, the terms "introgression", "introgressed" and "introgress" refer to the process by which one or more genetic elements such as a gene or genes, one or more QTLs, one or more alleles, one or more chromosomal fragments, or one or more nucleic sequences present in the genome of a species, a variety or a cultivar are moved and transferred stably into the genome of another species, variety or cultivar, by sexual crossing. The transfer can be natural or artificial. The process can optionally be supplemented by backcrossing with a recurrent parent, in which case introgression refers to introduction of one or more genetic elements, such as one or more genes, one or more alleles, one or more QTLs, one or more chromosomal fragments or one or more nucleic sequences of one species into the gene pool of the other by repeated backcrossing of an interspecific hybrid with one parent thereof. Introgression can also be described as the stable integration of heterologous genetic material in the genome of a recipient plant by sexual crossing between plants of identical or similar, i.e. sexually compatible, species. The concept of sexual compatibility means that the fertilization of a flower of one plant by the pollen of another plant results in the fertilization of the ovule and the production of a fruit containing one or more seeds capable of germinating and of yielding a new plant. The concept of sexual compatibility also relates to cases where the viability of the embryo formed is ensured by one or more embryo rescue techniques. The skilled person has various embryo rescue methods which he can use according to the species concerned.

Thus proposed, according to a preferred embodiment of the present invention, is a method for increasing at least one phenotypic trait selected from biomass, germination rate, yield, in particular seed yield, abiotic stress resistance, biotic stress resistance, germination rate, growth, of a plant, comprising provision of a plant population, including the provision of a plant population arising from crosses, and selection of individuals of the population that exhibit the highest L-aspartate oxidase expression possible.

The plant population can be a population of mutant plants generated by chemical mutagenesis or any other means capable of inducing one or more mutations in the genome of plants thus treated. The mutagenesis treatment results in the voluntary introduction of mutations by the action of chemical or physical mutagenic agents in a DNA sequence, agents that can be a chemical treatment such as, for example, treatment with ethylmethanesulfonate (EMS).

Advantageously, a TILLING population can be used to select individuals that have the highest L-aspartate oxidase expression possible.

Typically, TILLING technology is based on mutagenesis of seeds followed by phenotyping and genotyping in order to identify the mutations and thus the alleles associated with a given phenotype, preferably an advantageous phenotype. The TILLING population can be generated as follows. M0 seeds are mutagenized by treatment with ethylmethanesulfonate (EMS). M1 plants resulting from M0 seeds are self-fertilized, M2 family DNA is extracted for high-throughput mutational screening and M3 seeds are collected and preserved. M2 family DNA is pooled eight times and amplified for a target gene. Amplification products are incubated with an endonuclease that preferably cleaves mismatches in heteroduplexes between wild-type and mutant. Digestion products are subjected to sequencing gel electrophoresis. LI-COR technology enables double-stranded fluorescent labeling (IRDye 700 and 800) which enables rapid visual confirmation because mutations are detected on the two complementary strands and thus easily distinguished from artifacts. Upon detection of a mutation in a pool, individual family DNA is rapidly screened by deconvolution of the pool in order to identify the family carrying the mutation.

In a particular embodiment of the present invention, introgression of a genetic element encoding overexpression of L-aspartate oxidase is produced by protoplast fusion.

Thus in such an embodiment of the invention, in order to increase at least one phenotypic trait selected from biomass, germination rate, yield, in particular seed yield, abiotic stress resistance, biotic stress resistance, germination rate, growth, protoplast fusion can be used to transfer at least one genetic element from a donor plant to a recipient plant. Protoplast fusion is an induced or spontaneous union, such as somatic hybridization, between two or more protoplasts (cell walls are removed by enzymatic treatment) in order to produce a single bi- or multinucleate cell. The fused cell, which can also be produced with plant species that cannot be sexually crossed in nature, is cultivated in a hybrid plant having the combination of desirable traits. More precisely, a first protoplast can be produced from a plant according to the invention that exhibits at least one phenotypic trait selected from biomass, germination rate, yield, in particular seed yield, abiotic stress resistance, biotic stress resistance, germination rate, growth and overexpression of L-aspartate oxidase. A second protoplast can be produced from a plant that has characteristics of commercial value. The protoplasts are then fused by means of conventional protoplast fusion procedures, which are known in the art.

Alternatively, embryo rescue can be used to transfer a genetic element, in particular a nucleic acid enabling overexpression of L-aspartate oxidase, from a donor plant according to the invention to a recipient plant according to the invention. Embryo rescue can be used as a procedure for isolating embryos from crosses in which the plants are unable to produce viable seeds. In this process, the plant's fertilized or immature ovule is culture tissue for creating new plants.

It is thus an object of the present invention to provide a method in which introgression of a genetic element encoding overexpression of L-aspartate oxidase is produced by embryo rescue.

The present invention also relates to a method for producing plants exhibiting at least one improved phenotypic trait selected from biomass, germination rate, yield, in particular seed yield, abiotic stress resistance, biotic stress resistance, germination rate, growth, comprising detection of the presence of a genetic element, in particular a nucleic acid sequence, linked to overexpression of L-aspartate oxidase in a donor plant, and transfer of the genetic element, in particular a nucleic acid sequence, linked to overexpression of the L-aspartate oxidase thus detected, from the donor plant to a recipient plant. The transfer of the nucleic acid sequence can be carried out by any of the methods previously described herein.

The transfer can be carried out by a technique selected from transgenesis, introgression, protoplast fusion, embryo rescue.

An example embodiment of such a method comprises transfer by introgression of the genetic element, in particular the nucleic acid sequence, linked to overexpression of L-aspartate oxidase from a donor plant to a recipient plant by sexual crossing of the plants. This transfer can thus advantageously be carried out using conventional crossing and selection techniques.

In a particular embodiment of the method according to the invention, detection of the presence of a genetic element linked to overexpression of L-aspartate oxidase is carried out using at least one molecular marker.

In another embodiment of the method according to the invention, detection of the presence of the genetic element linked to overexpression of L-aspartate oxidase is carried out by measuring L-aspartate oxidase enzymatic activity in the donor plant.

According to certain embodiments, the genetic element responsible for overexpression of L-aspartate oxidase can be introgressed into commercial varieties of plants of agronomic interest using marker-assisted selection (MAS), which involves the use of one or more molecular markers for the identification and selection of progeny plants that contain the genetic element, the gene or plurality of genes, the nucleic acid sequences encoding the desired characteristic of L-aspartate oxidase overexpression.

In the context of the present invention, such an identification and such a selection are based on the selection of genes, genetic elements or nucleic acid sequences or markers that are associated therewith.

Plants produced according to these embodiments can advantageously draw the majority of their traits from the recipient plant, and draw at least one phenotypic trait selected from increased biomass, increased germination rate, increased yield, in particular increased seed yield, increased abiotic stress resistance, increased biotic stress resistance, increased germination rate, increased growth of the donor plant, by virtue of overexpression of L-aspartate oxidase.

As discussed above, conventional crossing techniques can be used for introgression of the nucleic acid sequence responsible for overexpression of L-aspartate oxidase linked to at least one phenotypic trait selected from increased biomass, increased germination rate, increased yield, in particular increased seed yield, increased abiotic stress resistance, increased biotic stress resistance, increased germination rate, increased growth in a recipient plant.

In certain embodiments, a donor plant that exhibits at least one phenotypic trait selected from increased biomass, increased germination rate, increased yield, in particular increased seed yield, increased abiotic stress resistance, increased biotic stress resistance, increased germination rate, increased growth and comprising a nucleic acid sequence responsible for overexpression of L-aspartate oxidase is crossed with a recipient plant which, in certain embodiments, can exhibit commercially desirable characteristics.

The resulting plant population (representing F1 hybrids) is then self-fertilized producing F2 seeds. F2 plants from F2 seeds are then screened in order to identify plants exhibiting overexpression of L-aspartate oxidase, associated with at least one phenotypic trait selected from increased biomass, increased germination rate, increased yield, in particular increased seed yield, increased abiotic stress resistance, increased biotic stress resistance, increased germination rate, increased growth, by methods known to the skilled person.

Measurement of L-aspartate oxidase expression or overexpression 1.0 can be carried out by various means at the disposal of the skilled person such as RNA-Seq, Northern blot, quantitative and semi-quantitative PCR, Western blot, ELISA or measurement of enzymatic activity, for example.

Plant lines exhibiting overexpression of L-aspartate oxidase, associated with at least one phenotypic trait selected from increased biomass, increased germination rate, increased yield, in particular increased seed yield, increased abiotic stress resistance, increased biotic stress resistance, increased germination rate, increased growth, can be developed using techniques of recurrent selection and backcrossing, self-fertilization, and/or doubled haploids, or any other technique used to make parental lines. In a recurrent selection and backcrossing process, increased expression of L-aspartate oxidase, associated with at least one phenotypic trait selected from biomass, germination rate, yield, in particular seed yield, abiotic stress resistance, biotic stress resistance, germination rate, growth, can be introgressed into a target recipient plant (the recurrent parent) by crossing the recurrent parent with a first donor plant, which differs from the recurrent parent and which is called herein the "non-recurrent parent". The recurrent parent is a plant that does not exhibit overexpression of L-aspartate oxidase, associated with at least one phenotypic trait selected from increased biomass, increased germination rate, increased yield, in particular increased seed yield, increased abiotic stress resistance, increased biotic stress resistance, increased germination rate, increased growth, but can have desirable commercial characteristics.

The non-recurrent parent can be any plant variety or pure line that is sexually compatible with the recurrent parent.

The progeny plants of crosses between the recurrent parent and the non-recurrent parent are backcrossed to the recurrent parent. The resulting plant population is then screened for overexpression of L-aspartate oxidase, associated with at least one phenotypic trait selected from increased biomass, increased germination rate, increased yield, in particular increased seed yield, increased abiotic stress resistance, increased biotic stress resistance, increased germination rate, increased growth.

Marker-assisted selection (MAS) can be implemented using hybridization probes or polynucleotides, in order to identify plants that comprise a nucleic acid sequence or any genetic element leading to overexpression of L-aspartate oxidase, associated with at least one phenotypic trait selected from increased biomass, increased germination rate, increased yield, in particular increased seed yield, increased abiotic stress resistance, increased biotic stress resistance, increased germination rate, increased growth.

Following screening, F1 hybrid plants that exhibit overexpression of L-aspartate oxidase, associated with at least one phenotypic trait selected from increased biomass, increased germination rate, increased yield, in particular increased seed yield, increased abiotic stress resistance, increased biotic stress resistance, increased germination rate, increased growth, are then selected and backcrossed to the recurrent parent for a certain number of generations in order to allow the plant to become increasingly inbred. This process can be carried out for two, three, four, five, six, seven, eight, or more generations.

Generally, the present invention relates to a method for producing a plant exhibiting at least one phenotypic trait selected from increased biomass, increased germination rate, increased yield, in particular increased seed yield, increased abiotic stress resistance, increased biotic stress resistance, increased germination rate, increased growth, which can comprise:
   (a) providing a plant having a given level of expression of L-aspartate oxidase;
   (b) providing a second plant having a higher level of expression of L-aspartate oxidase than that of the plant provided in (a);
   (c) carrying out crossing of the plant provided in (a) with the plant provided in (b), to produce F1 progeny plants;
   (d) selecting F1 progeny plants that exhibit overexpression of L-aspartate oxidase in relation to the plant provided in (a);
   (e) crossing plants selected in (d) with the plant provided in (a) to produce backcrossed progeny plants;
   (f) selecting backcrossed progeny plants that exhibit overexpression of L-aspartate oxidase in relation to the plants selected in (d);
   (g) repeating steps (e) and (f) two or more times in succession;
   (h) optionally self-fertilizing plants resulting from backcrossing in order to identify homozygous plants, and
   (i) carrying out crossing of at least one backcrossed progeny plant or self-fertilized plants with another plant provided in (a) to produce a plant exhibiting at least one phenotypic trait selected from increased biomass, increased germination rate, increased yield, in particular increased seed yield, increased abiotic stress resistance, increased biotic stress resistance, increased germination rate, increased growth when cultivated under the same environmental conditions.

As indicated, the last backcrossed generation can be self-fertilized in order to provide homozygous individuals exhibiting overexpression of L-aspartate oxidase and at least one phenotypic trait selected from increased biomass, increased germination rate, increased yield, in particular increased seed yield, abiotic stress resistance, increased biotic stress resistance, increased germination rate, increased growth.

In accordance with a preferred embodiment of the present invention, the selection step comprises selection of individuals each of which contains an allele of the gene that encodes overexpression of L-aspartate oxidase.

The present invention also relates to a method for selecting a plant, characterized in that it comprises searching for an allele of the L-aspartate oxidase enzyme gene having a mutation resulting in an improvement in at least one phenotypic trait selected from biomass, germination rate, yield, in particular seed yield, abiotic stress resistance, biotic stress resistance, germination rate, growth.

In addition, according to a preferred embodiment of the present invention, the selection step comprises selection using a molecular marker for the allele of the L-aspartate oxidase gene.

Furthermore, according to a preferred embodiment of the present invention, the selection step comprises selection by measuring L-aspartate oxidase enzyme activity in young plants and selecting those exhibiting high enzyme activity.

In a particular embodiment, the invention relates to a method for selecting a plant exhibiting overexpression of L-aspartate oxidase, comprising the following steps:
   (a) providing a plant population;
   (b) measuring the L-aspartate oxidase activity of each individual of the plant population provided;
   (c) selecting plants exhibiting the highest L-aspartate oxidase activity.

In a particular embodiment, the plant population is a TILLING population.

In another particular embodiment, the plant population is a population resulting from intraspecific or interspecific crosses.

In another particular embodiment, the plant population is a population of commercial varieties.

In the context of the present invention, the expression "overexpression" in reference to L-aspartate oxidase refers to the fact that the DNA nucleic sequence encoding the protein is transcribed into RNA in increased amounts and/or that the RNAs of the protein are translated into protein in increased amounts and/or that the amount or the specific activity of the translated protein is increased. Measurement of this "overexpression" can be evaluated in terms of both the level of RNA and the level of proteins by various means at the disposal of the skilled person such as RNA-Seq, Northern blot, quantitative and semi-quantitative PCR, Western blot, ELISA or measurement of enzymatic activity, for example. Finally, the concept of expression or overexpression refers to L-aspartate oxidase enzymatic activity in the plant, due to greater synthesis of the protein and/or to higher specific activity.

In the context of the present invention, the expressions "sexual crossing" and "sexual reproduction" refer to fusion of gametes in order to produce progeny (for example by fertilization, so as to produce seeds by plant pollination). "Sexual crossing" or "cross-fertilization" is, in certain embodiments, fertilization of an individual by another (for example, plant cross-pollination). The term "self-fertilization" refers, in certain embodiments, to seed production by self-fertilization or self-pollination, i.e. pollen and ovules are from the same plant.

By the expression "trait", in the present context, is meant a characteristic or a phenotype, for example yield, biomass or germination rate. A trait can be inherited in a dominant or recessive manner, or can be monogenic or polygenic.

By the expression "donor plant", in the context of the invention, is meant a plant that provides at least one genetic element linked to overexpression of L-aspartate oxidase.

By the expression "recipient plant", in the context of the present invention, is meant a plant that receives at least one genetic element linked to overexpression of L-aspartate oxidase.

In the context of the present invention, the expressions "genetic marker", "DNA marker" and "molecular marker" are interchangeable and refer to a characteristic of the genome of an individual (for example a nucleotide or a nucleic acid sequence present in the genome of an individual), which is linked to one or more loci of interest. Genetic markers include, for example, single nucleotide polymorphisms (SNPs), indels (i.e. insertions/deletions), simple sequence repeats (SSRs), restriction fragment length polymorphisms (RFLPs), amplified fragment length polymorphisms (AFLPs), for example. Genetic markers can, for example, be used to locate genetic loci containing alleles that contribute to the variability of phenotypic characteristics. The expression "genetic marker" can also refer to a polynucleotide sequence complementary to a genomic sequence, such as a nucleic acid sequence used as a probe. A genetic or molecular marker can be physically located in a position on a chromosome that is distal or proximal in relation to one or more genetic loci with which it is linked (i.e. is intragenic or extragenic, respectively). In certain embodiments of the present invention the one or more genetic markers comprise between one and ten markers, and in certain embodiments the one or more genetic markers comprise more than ten genetic markers.

In the context of the present invention, the term "genotype" refers to the genetic makeup of a cell or an organism. As is known in the art, a genotype can relate to a single locus or to multiple loci. In certain embodiments, the genotype of an individual relates to one or more genes that are linked by the fact that one or more genes are involved in the expression of a phenotype of interest (for example a trait as defined herein). Thus, in certain embodiments, a genotype comprises one or more alleles present in an individual at one or more loci for a trait.

In the context of the present invention, the term "gene" refers to a hereditary unit comprising a DNA sequence that occupies a specific location on a chromosome and that contains the genetic instructions for a particular characteristic or trait in an organism.

In the context of the present invention, the terms "nucleic acid" or "oligonucleotide" or "polynucleotide" or "nucleic sequence" or grammatical equivalents thereof mean at least two nucleotides joined together covalently. Oligonucleotides are typically about 7, 8, 9, 10, 12, 15, 25, 18, 20, 30, 40, 50 or up to about 100 nucleotides in length. Nucleic acids, nucleic sequences and polynucleotides are polymers of any length, including the longest lengths, for example 200, 300, 500, 1000, 2000, 3000, 5000, 7000, 10000, etc. A nucleic acid of the present invention will generally contain phosphodiester bonds, although in certain cases nucleic acid analogues are included, which can have alternative backbones comprising, for example, phosphoramidate, phosphorothioate, phosphorodithioate, or O-methylphosphoramidite bonds (see Eckstein, 1991), and peptide backbones and nucleic acid bonds. Mixtures of natural nucleic acids and analogues can be used.

In the context of the present invention, the expression "phenotype" or "phenotypic trait" refers to the appearance or any other detectable characteristic of an individual, resulting from the interaction of the genome, proteome and/or metabolome thereof with the environment.

In the context of the present invention, a "plant" is a plant at any stage of development, in particular a seed plant.

In the context of the present invention, a "plant cell" is a structural and physiological unit of a plant, comprising a protoplast and a cell wall. The plant cell can be in the form of an isolated single cell or a cultivated cell, or as part of a higher organized unit such as, for example, a plant tissue, a plant organ or a whole plant. A plant cell may be able to regenerate a plant or may not be able to regenerate a plant.

In the context of the present invention, the expression "plant material" refers to leaves, stems, roots, flowers or flower parts, fruits, pollen, ovules, zygotes, seeds, cuttings, cell or tissue cultures, or any other part, or products of a factory.

As used herein, the expression "plant part" refers to a part of a plant, comprising single cells and cellular tissues such as plant cells that are intact in plants, cell clusters, and tissue cultures from which plants can be regenerated or not. Examples of plant parts include, but are not limited to, individual cells and tissues of pollen, ovules, leaves, embryos, roots, root tips, anthers, flowers, fruits, stems, shoots and seeds, as well as grafts, rootstocks, protoplasts, calluses, and the like.

As used herein, the term "population" refers to a genetically heterogeneous set of plants sharing a common genetic derivation.

In the context of the present invention, "biomass" means all of the organic matter produced by a plant. This biomass can be measured in fresh weight, in dry weight per plant or per $m^2$, for example. Alternatively, biomass can be evaluated by the size of the plant or the number of leaves, for example.

In the context of the present invention, the expression "germination rate" corresponds to the average time between the imbibition of the seed and the emergence of the radicle from the seed coat.

In the context of the present invention, the expression "yield" refers to the amount of commercial plant matter produced by the crop plant per unit area, for a given planting density if need be.

In the context of the present invention, the expression "seed yield" represents the amount of seeds, by weight or by number, produced by the crop plant per unit area or per plant, for a given planting density if need be.

In the context of the present invention, the expression "biotic stress resistance" refers to the plant's ability to deal with and to combat stress that occurs following damage caused to said plant by other living organisms, such as bacteria, viruses, fungi, parasites, beneficial and harmful insects, weeds and other crop or indigenous plants. Damage caused by these various living agents can appear very similar and affects crop plant growth and yield.

In the context of the present invention, the expression "abiotic stress resistance" refers to the plant's ability to deal with and to combat stress induced by non-living factors in a specific environment. Abiotic stress factors are of natural origin, often intangible, factors such as intense sunlight, or lack of light, excess or insufficient water, cold or excessive heat, salinity or wind, for example, which can cause damage to plants in the affected area. Abiotic stress is essentially inevitable and particularly restrictive for plants. Abiotic stress is the factor most harmful to crop growth and productivity worldwide.

In the context of the present invention, the expression "growth" refers to the difference in the biomass of the plant concerned between emergence and harvest per unit time under given sunlight, irrigation and input conditions.

FIGURES

EXAMPLES

Materials and Methods

Generation of Transgenic Plants

Figure 1:
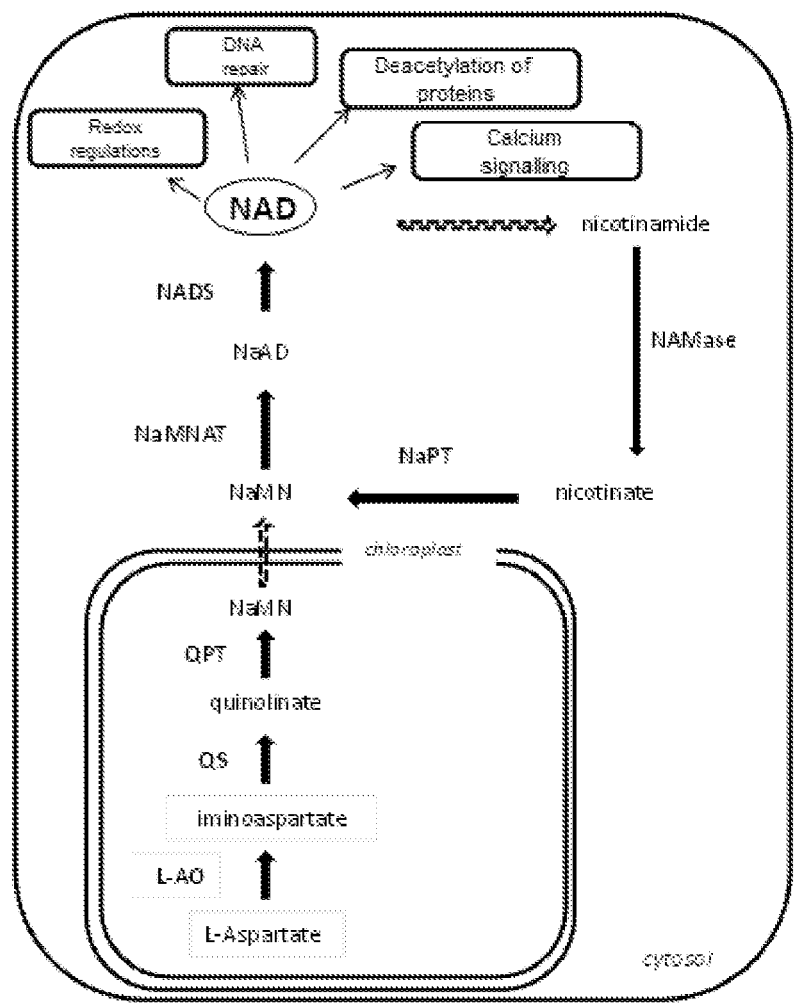
FIG. 1 is a description of the NAD biosynthesis pathway in plants, and the use thereof for energy metabolism and stress-related signaling (L-aspartate oxidase (AO) activity is shown in the figure).
Figure 2:
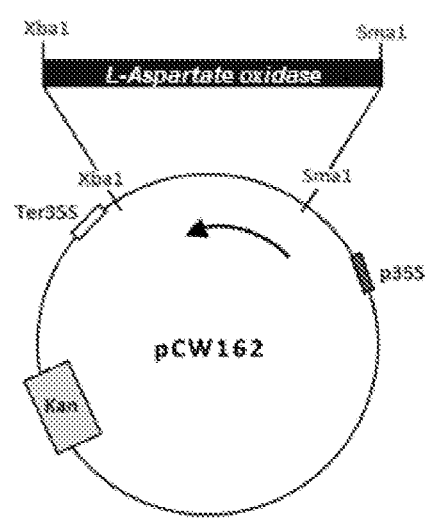
FIG. 2 is a schematic representation of the construction of a plant transformation vector, pCW162, comprising the L-aspartate oxidase (AO) overexpression cassette.

*Arabidopsis thaliana* cDNA (coding sequence, CDS) encoding L-aspartate-oxidase (L-AO) (SEQ ID NO: 1) was amplified by PCR with primers having the following sequences:

```
sense primer                    (SEQ ID NO: 17)
(GAG AGA CCC GGG ATG GCG GCT CAT GTT TCT AC);
```

```
antisense primer                (SEQ ID NO: 18)
(GAG AGA CAG CTG AAT CGT TAG TTA TTC ACT CGA C);
```

The amplification product was then subcloned between the Sma1 and Sal1 sites of the binary vector pCW162, under the control of the CaMV35S promoter in order to generate transgenic plants overexpressing L-aspartate oxidase. The nptII cassette of pCW162 was used for the selection of transgenic plants on medium containing kanamycin. The resulting plasmid was then used for the stable transformation of *Arabidopsis thaliana* plants in order to overexpress the L-AO gene, using *Agrobacterium tumefaciens* strain GV3101. Primary transformants were selected on Murashige and Skoog medium containing 50 mg/l kanamycin monosulfate. After about 10 days of culture in vitro (23° C., under light intensity of 100 μmol of photons/m$^2$/s), resistant seedlings were transferred to containers of potting soil in a long-day (LD: 16-hour day, 8-hour night) culture chamber in order to produce seeds that have undergone a new selection scheme. The number of putative transgenic plants was noted in order to select lines that inserted a single copy of the transgene (ratio of ¾ non-resistant, ¼ resistant). Progeny were selected until stable lines homozygous for the T-DNA insertion were obtained.

Measurement of Levels of L-Aspartate Oxidase Transcripts

After a total RNA extraction using the NucleoSpin RNA II kit (Macherey-Nagel) according to the supplier's instructions, 1 μg of total RNA was used as template for synthesis of first-strand cDNA and reverse transcription with the first-strand synthesis system SuperScript III (Invitrogen). Overexpression of the L-aspartate oxidase gene was examined by RT-PCR with primers having the following sequences:

```
sense primer                    (SEQ ID NO: 19)
(GAT CGT TCA CCG TGC TGA TA)
and antisense primer                (SEQ ID NO: 20)
(TGT GTT CAA GCC ATC CTG AG)
```

The control (ctrl) line, or plant, was produced from ecotype Columbia (Col 0) transformed with the empty vector pCW1628.

Plant Culture

The transgenic lines of *Arabidopsis thaliana* used in this study were produced from *Arabidopsis thaliana* ecotype Columbia plants (Col 0). After 48 hours of stratification at 4° C. in the dark, the seeds were sown and cultivated under short-day (SD: 8-hour day, 16-hour night) conditions in a culture chamber under illumination of 100 μmol photons/m$^2$/s at the leaf, at 18-20° C. and 65% humidity (except for the determination of silique number and the measurement of seed amount, long-day (LD: 16-hour day, 8-hour night) conditions were used). Nutrient solution was supplied twice per week.

Sampling for Metabolic Analyses

Leaf samples were taken in the middle of the photoperiod, rapidly frozen in liquid nitrogen and stored at −80° C. until subsequent analysis. For metabolomic and transcriptomic analyses, the plants were analyzed and sampled at 6 weeks of age (SD), and at 8 weeks of age (SD) for gas-exchange analysis.

Assay of L-Aspartate Oxidase Activity

A method for assaying L-aspartate oxidase activity was developed using a spectrophotometer: 0.5 g of a sample of frozen leaves was ground in liquid nitrogen and taken up in 2 ml of extraction buffer (Tris-HCl, pH 8). After centrifugation, the crude extract was desalted by size-exclusion chromatography on a PD10 column. For 0.7 ml of desalted extract, 100 µl of 10 mM L-aspartate, 100 µl of 10 mM fumarate and 100 µl of 200 µM FAD were added to start the reaction, which was followed at 30° C. for 30 minutes. The reaction was stopped by heating at 100° C. for 2 minutes in order to precipitate the proteins, followed by centrifugation. To 1 ml of reaction supernatant were successively added:

0.5 ml of 0.33 M sodium phenolate, pH 13;
0.5 ml of 0.1% sodium nitroprusside;
0.5 ml of 0.2% NaClO.

L-Aspartate oxidase activity was measured by spectrophotometry at OD 635 nm by assay, against a standard range of 0 to 100 nmol of $(NH_4)SO_4$, $NH_4^+$ coming from the near instantaneous degradation at pH 8 of the iminoaspartate formed during the reaction.

Metabolomic Measurements

Assays of metabolites with antioxidant properties, such as the pyridine nucleotides $NAD^+$ and NADH, were carried out by spectrophotometry via enzymatic coupling on a microplate reader. These metabolites were quantified by a recycling reaction by following the reduction of DCPIP (2,6-dichlorophenol-indophenol) at 600 nm in the presence of alcohol dehydrogenase and ethanol. $NAD^+$ is assayed after acid extraction: About 100 mg of leaves was ground with a mortar in liquid nitrogen, to which 1 ml of 0.2 N HCl is added. After the ground material was thawed, it was transferred to a 2 ml Eppendorf tube. The extract is then clarified by centrifugation for 10 minutes at 14,000 g, at 4° C. 200 µl of supernatant was heated for 1 minute at 100° C., then neutralized by adding 20 µl of $NaH_2PO_4$ (200 mM, pH 5.6) and a sufficient volume of 0.2 M NaOH (about 200 µl) to reach pH 7. For the assay of NADH, alkaline extraction was necessary. In the same manner as for the acid extraction, 100 mg of leaves was ground with a mortar in liquid nitrogen then 1 ml of 0.2 M NaOH was added. The mixture was then centrifuged for 10 minutes at 14,000 g at 4° C. 200 µl of supernatant was heated for 1 minute at 100° C., then neutralized by adding 20 µl of $NaH_2PO_4$ (200 mM, pH 5.6) and a sufficient volume of 0.2 N HCl (about 150 µl) to reach pH 7.

Spectrophotometric measurement of the extracted metabolites is carried out as follows: In each measurement well were successively added 100 µl of 100 mM HEPES/2 mM EDTA buffer (pH 7.5), 20 µl of 1.2 mM DCPIP, 10 µl of 10 mM PMS (phenazine methosulfate) and 10 µl of ADH (25 U) in a final volume of 200 µl. For the test samples, 20 µl of extract and 25 µl of double-distilled water are added. After shaking the plate, the reaction is initiated by adding 15 µl of absolute EtOH. NAD measurements are carried out at 600 nm by a microplate reader in reference to a standard range of $NAD^+$ or of NADH.

The ATP assay was carried out using the ENLITEN ATP Assay System Bioluminescence kit (Promega) following the procedure recommended by the supplier.

Measurements of Gas Exchange

Measurements of gas exchange and of chlorophyll fluorescence were carried out using the LI-6400XT system (LI-COR, Lincoln, Nebr., USA) and the parameters were calculated with the software provided by the manufacturer. The conditions were: photon flux density IA 1,000 mmol $m^2$/s, chamber temperature 22° C., flow rate 100 mmol/s, relative humidity 60%. The net carbon assimilation (An) responses and the molar fraction of internal $CO_2$ (An/Ci curves) carried out under ambient oxygen content conditions (21%) were measured on attached leaves with an infrared gas analysis system equipped with a fluorimeter chamber (LI-COR 6400-40; LI-COR Inc., Lincoln, Nebr., United States).

Germination Test

In order to ensure that the differences in germination rates observed are not due to seed quality, wild plants and mutant plants were cultivated side by side under identical conditions in a culture chamber in order to produce fresh seeds under long-day conditions. Fully mature and sterilized seeds were sown on plates of ¼ Hoagland's medium, nitrate-free (0.2 mM) or nitrate-rich (2.25 mM). After stratification for 2 days at 4° C. in the dark, the seeds were placed in a culture chamber at 23° C. Radicle protrusion was used as the criterion for evaluating germination differences between wild-type and mutant seeds.

Test for Resistance to Abiotic Stress Conditions

Seven-week-old plants cultivated under short-day (SD) conditions were transferred for one week under conditions of continuous light of 350 µmol photons/$m^2$/s at 37° C. and 65% humidity.

Test for Resistance to Biotic Stress

*Myzus persicae* aphids from the same colony maintained in the laboratory on wild *Arabidopsis thaliana* plants of the same ecotype as that of the wild and mutant plants tested were collected and transferred to fresh 5-week-old plants. In 2 days, they produced larvae. The adult aphids were removed and only the larvae were kept. This made it possible to produce aphids of the same age ±1 day. Seven days later, 3 aphids were transferred to each 18-day-old plant of each genotype. After 5 days, the number of aphids was counted with a magnifying glass for each plant. By statistical analysis (ANOVA), it was confirmed that rosette diameter did not influence aphid proliferation.

Statistical Analyses

Unless otherwise specified, the data are the means and standard deviations of three to five independent samples of different plants; significant differences are expressed using Student's t-test with $p<0.05$. All the experiments were repeated at least three times and gave similar results. The Student's t-test and the two-way analysis of variance (ANOVA) were implemented using the Excel software (Microsoft).

Results

Figure 3:
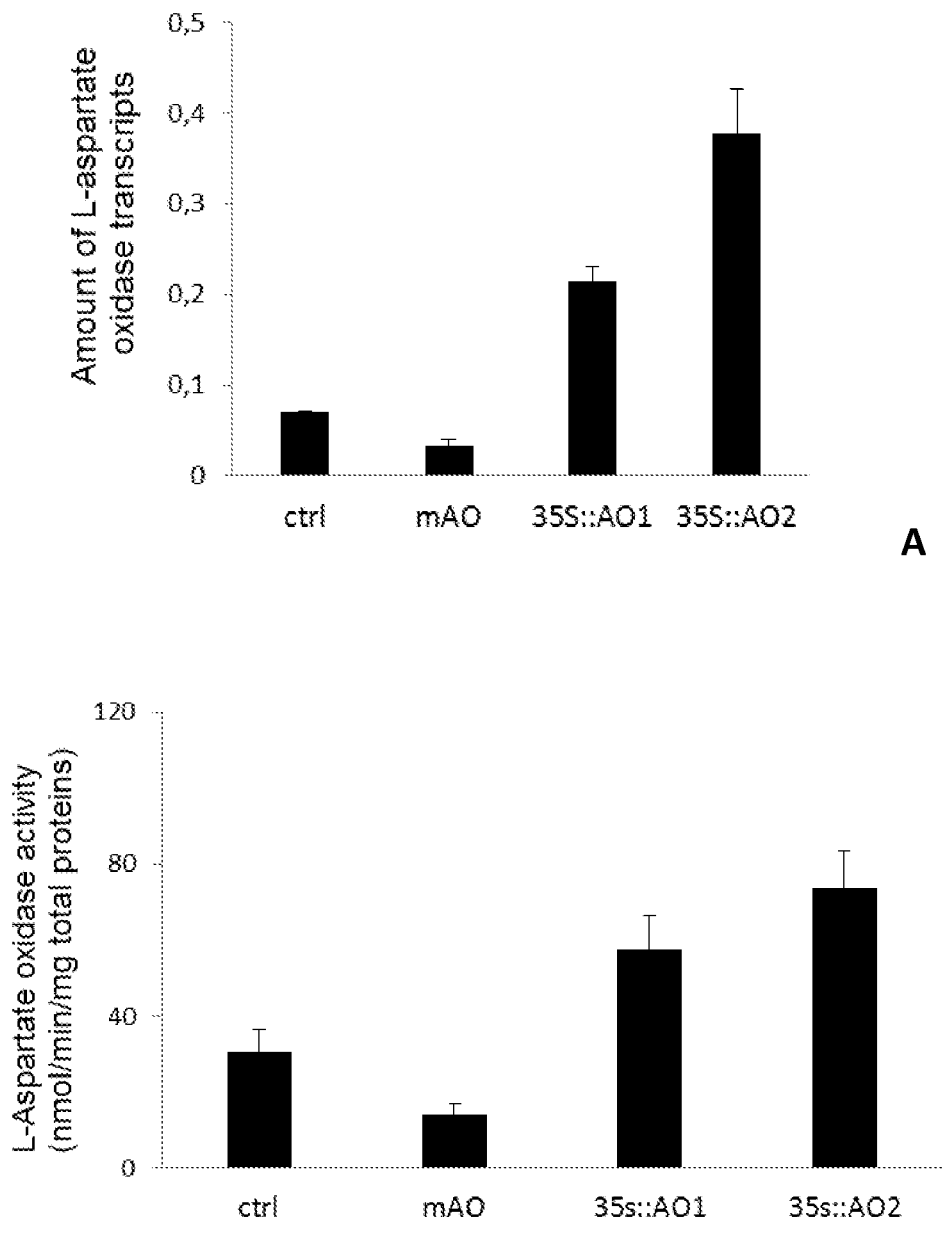
FIG. 3 is a graph representing the level of expression (A) and the activity (B) of L-aspartate oxidase in the leaves of control plants (ctrl), of plants overexpressing L-aspartate oxidase (35S::AO1 and 35S::AO2) and of plants mutant-negative for L-aspartate oxidase (mAO), 6 weeks of age.

The results indicate that the *Arabidopsis thaliana* nucleotide sequence used for transformation of the plants, and which is homologous to that of the bacterial L-aspartate oxidase characterized in the literature, indeed corresponds to L-aspartate oxidase activity and that the transformed lines exhibit L-aspartate oxidase activity that is increased by a factor of 2 to 4 (FIG. 3).

Figure 4:
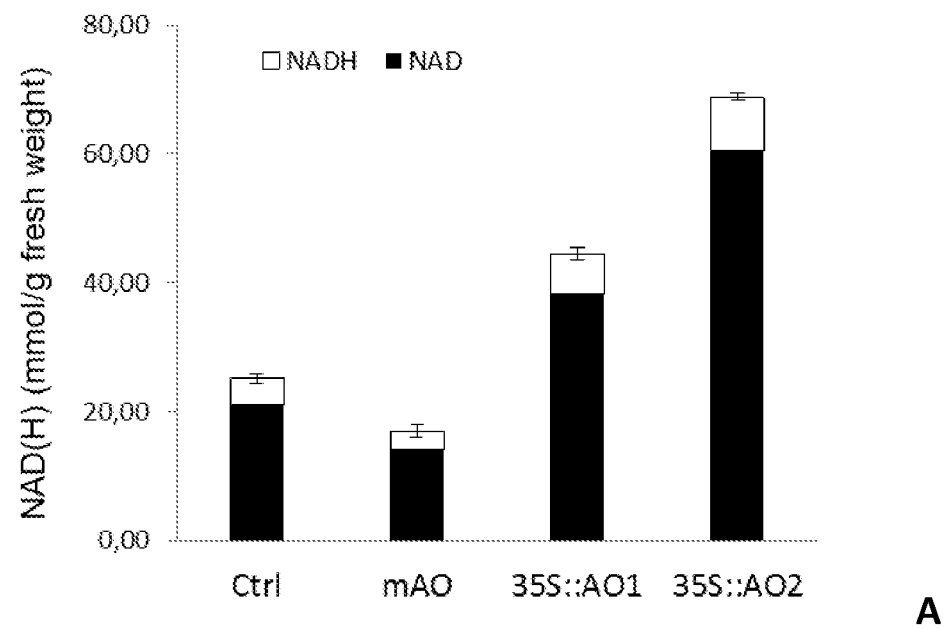
FIG. 4 is a graph representing energy-related metabolites (ATP (B) and pyridine nucleotides (A)) in the leaves of control plants (ctrl), of plants overexpressing L-aspartate oxidase (35S::AO1 and 35S::AO2) and of plants mutant-negative for L-aspartate oxidase (mAO), 6 weeks of age.
Figure 4:
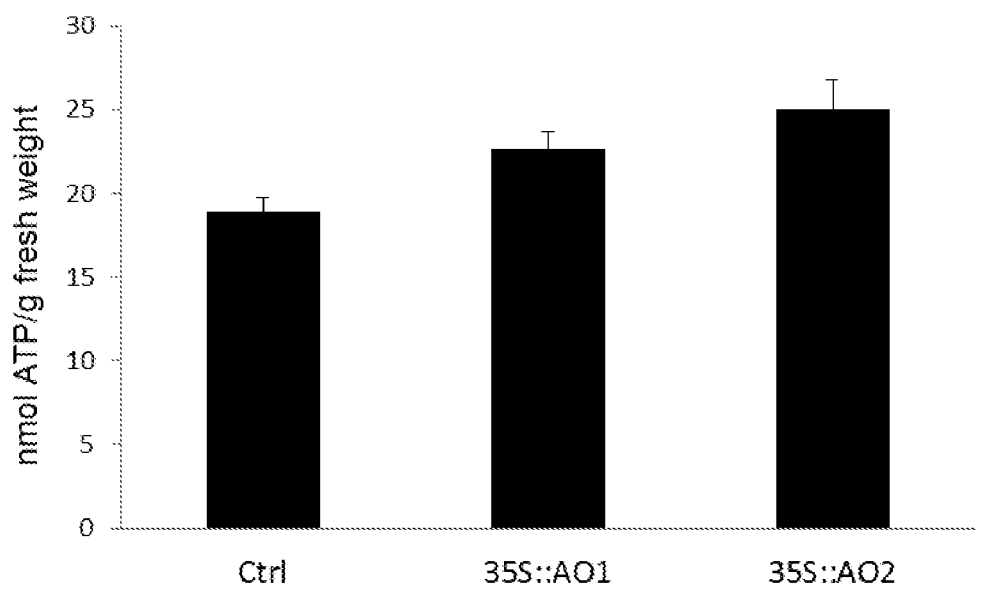

The results show that the constitutive overexpression of L-aspartate oxidase cDNA indeed leads to an increase in levels of NAD and of related energy metabolites (FIG. 4).

Figure 5:
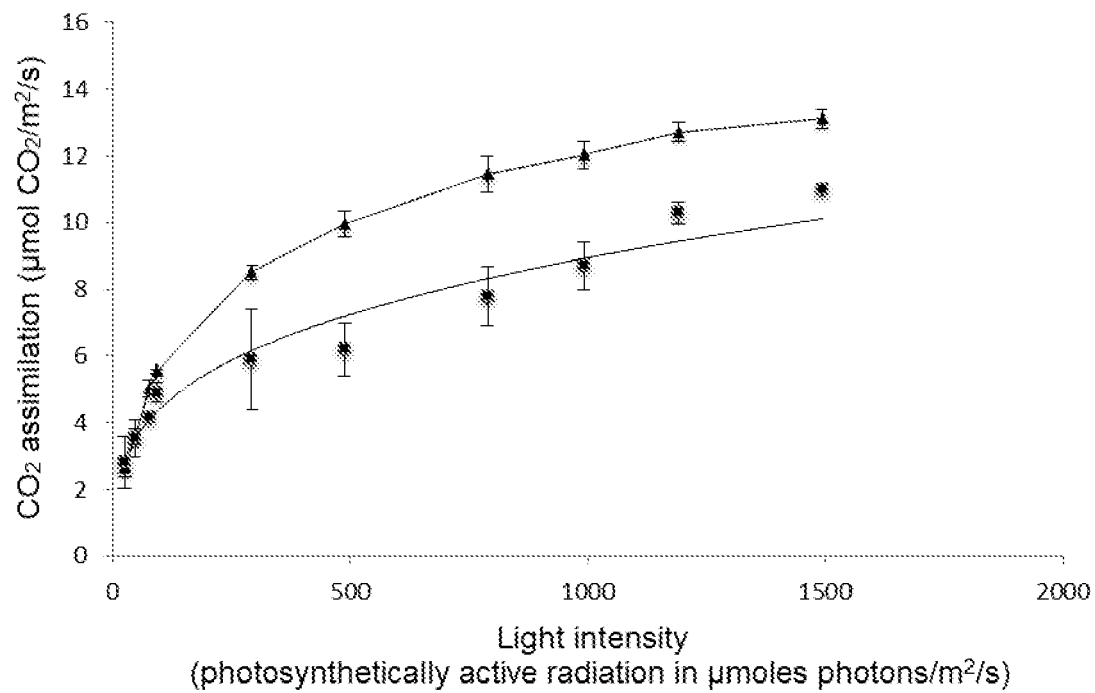
FIG. 5 represents the photosynthetic capacities of leaves of control plants (■) and of plants overexpressing (▲) L-aspartate-oxidase, 6 weeks of age.

The results show that lines overexpressing L-aspartate oxidase have higher rates of photosynthetic $CO_2$ assimilation (FIG. 5).

Figure 6:
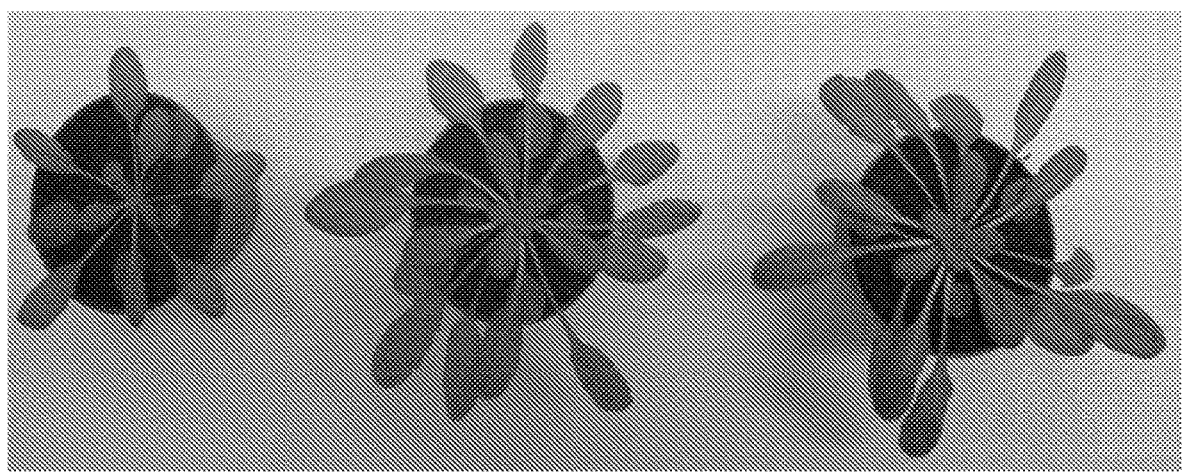
FIG. 6 is a photograph of control *Arabidopsis thaliana* plants and of plants overexpressing L-aspartate oxidase (35S::AO1 and 35S::AO2), 6 weeks of age.
Figure 7:
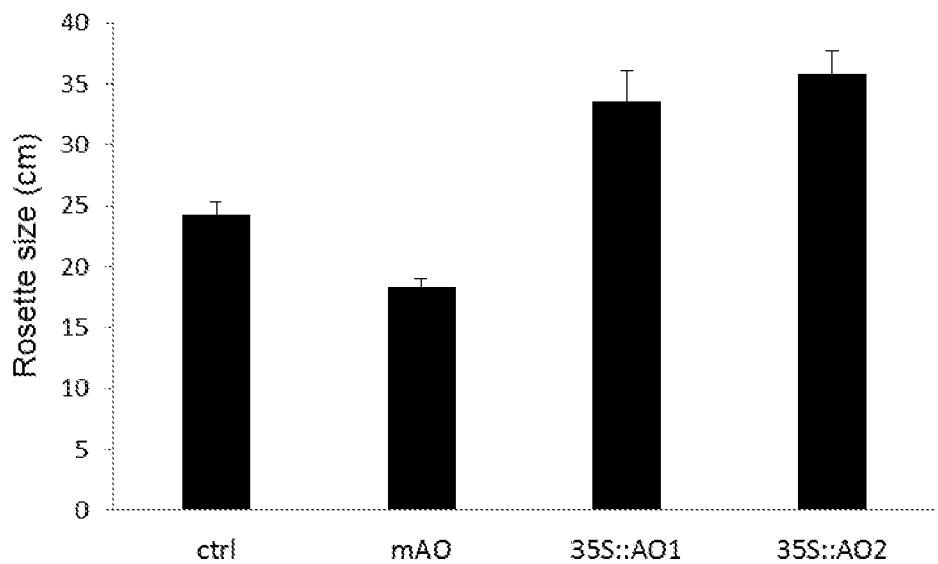
FIG. 7 is a graph representing the biomass (B) and the size (A) of control plants (ctrl), of plants overexpressing L-aspartate oxidase (35S::AO1 and 35S::AO2) and of plants mutant-negative for L-aspartate oxidase (mAO).
Figure 7:
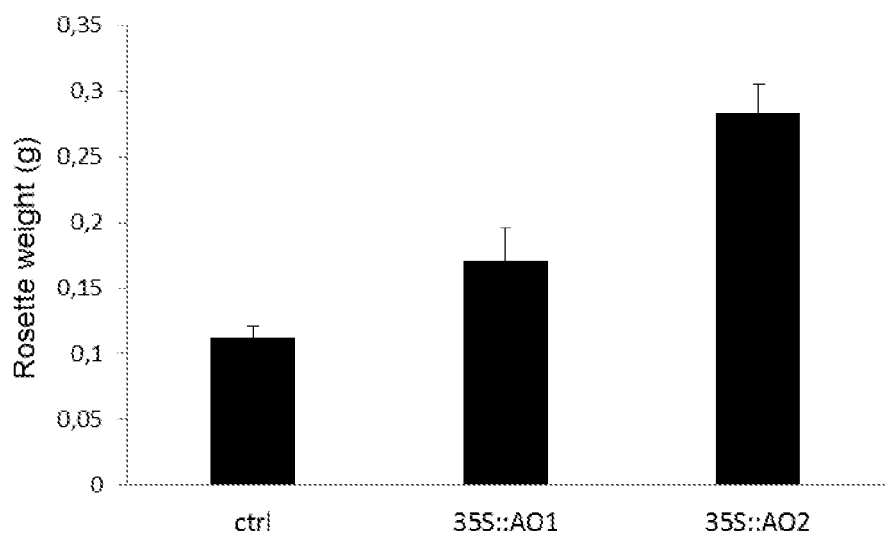
Figure 9:
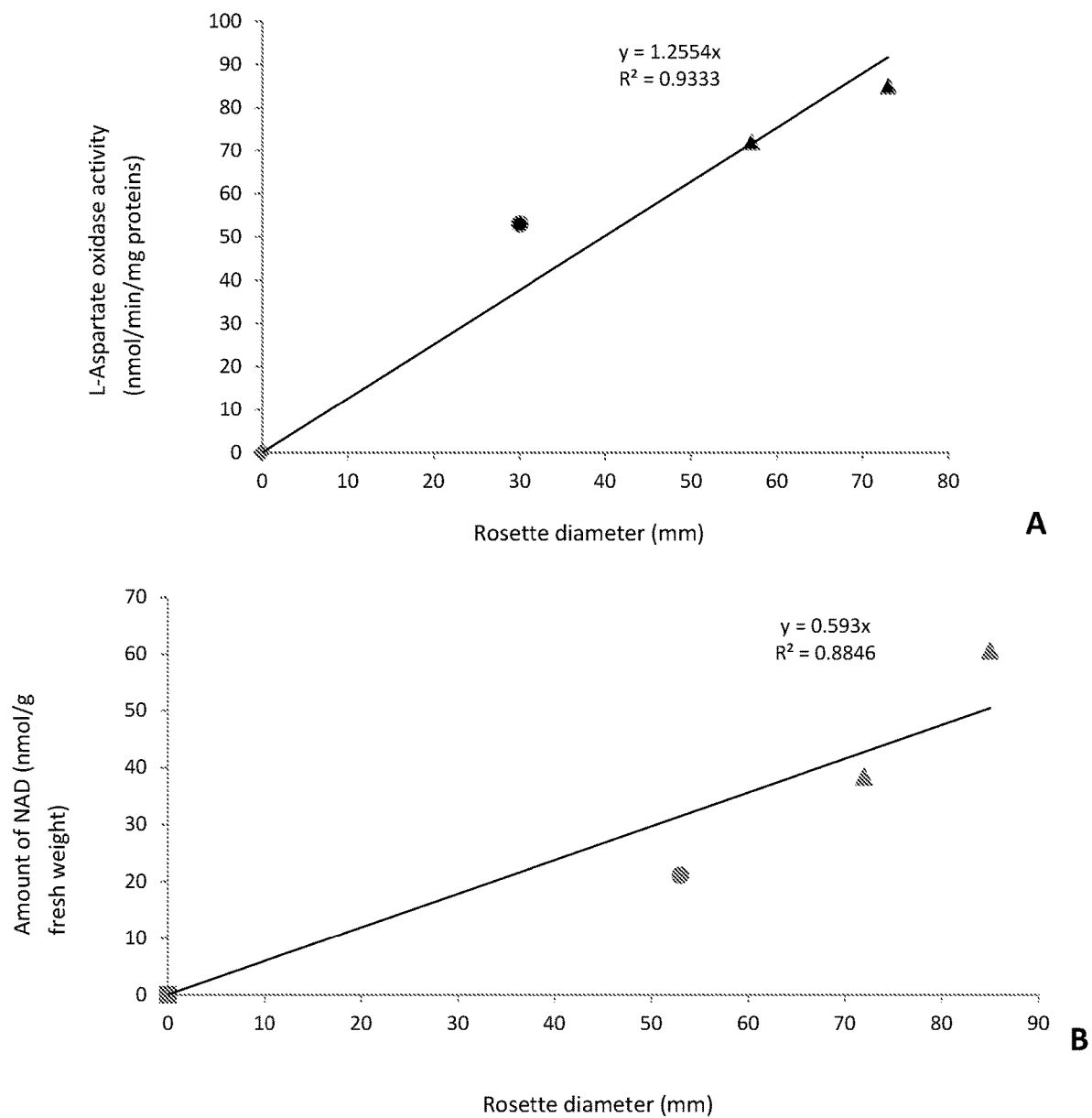
FIG. 9 is a graph representing the correlation between L-aspartate oxidase activity (A), NAD levels (B) and biomass expressed as rosette diameter.

The growth and the yield of plants transformed with the L-aspartate oxidase expression cassette were evaluated. Overexpression of L-aspartate oxidase leads to an increase in root growth and in leaf surface area. The size of transgenic plants overexpressing L-aspartate oxidase is larger than the size of control plants of the same age (FIGS. 6 and 7). The opposite is observed in mutant plants with greatly reduced levels of aspartate oxidase (FIG. 7). The fresh weight of the plantlets is also significantly increased (FIG. 7) and the ratio of fresh weight to dry weight is unchanged in relation to control plants. In addition to the plant's increased development, an increase in the mean size of epidermal cells can be detected. No ploidy variation was observed between plants overexpressing L-aspartate oxidase and plants not overexpressing L-aspartate oxidase, which confirms that the increased size of lines overexpressing L-aspartate oxidase is not linked to increased ploidy. A strong correlation between the diameter of the rosette and the abundance of transcripts, from the activity and level of L-aspartate oxidase and NAD, was observed (FIG. 9), showing that the increase in plant growth depends directly on the level of L-aspartate oxidase expression. Overexpression of L-aspartate oxidase thus causes an increase in cell growth and an increase in the growth and development of the entire plant.

Figure 8:
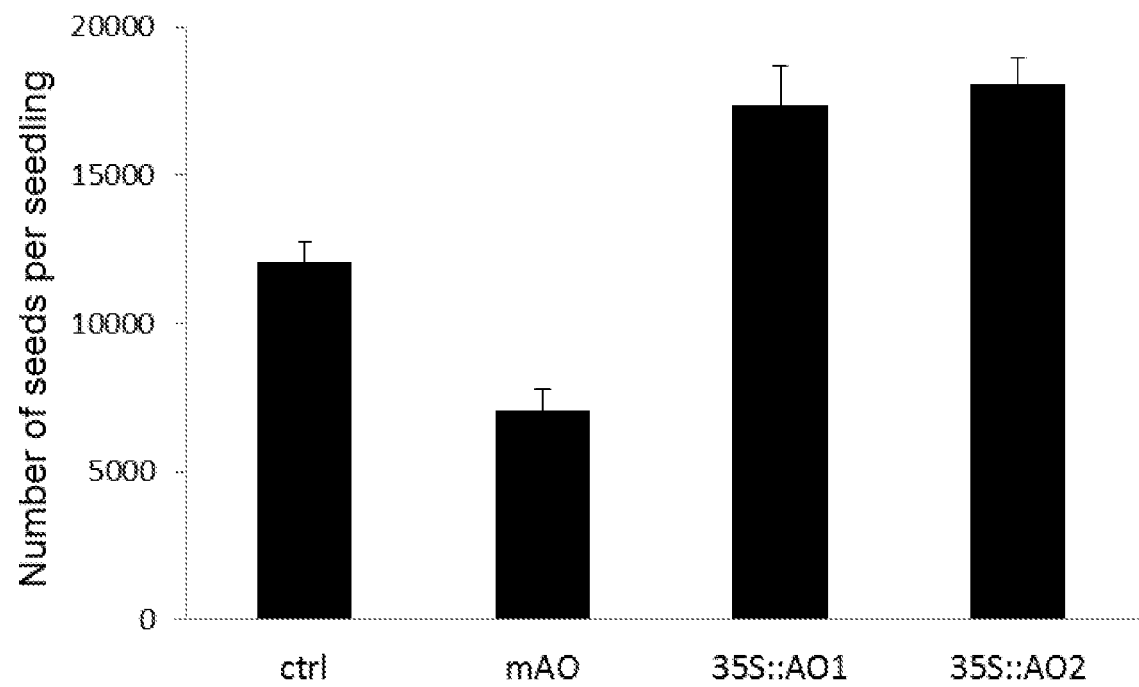
FIG. 8 is a graph representing the seed biomass collected from control plants (ctrl), from plants overexpressing L-aspartate oxidase (35S::AO1 and 35S::AO2) and from plants mutant-negative for L-aspartate oxidase (mAO).

The seed yield of transgenic plants overexpressing L-aspartate oxidase proves to be higher than that of control plants. The 45% increase in seed yield observed (FIG. 8) correlates with the number of siliques per plant. This increase in seed production is not accompanied by any silique-filling problem in plants overexpressing L-aspartate oxidase in relation to control plants. Furthermore, silique size is identical between all the plants. Overexpression of L-aspartate oxidase thus results in increased seed yield. Conversely, mutant plants with low L-aspartate-oxidase activity have a seed yield 42% lower than control lines.

Figure 11:
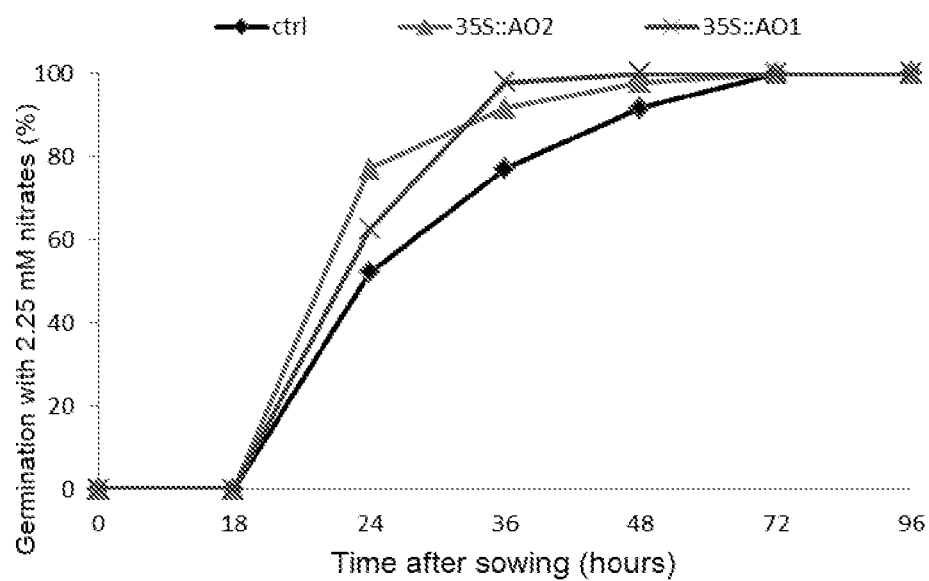
FIG. 11 is a germination curve for control plants (♦) and for plants overexpressing L-aspartate oxidase (35S::AO1 (■ and X) and 35S::AO2 (▲)) under nitrogen (nitrate)-rich medium conditions (A) and nitrogen (nitrate)-poor medium conditions (B).
Figure 11:
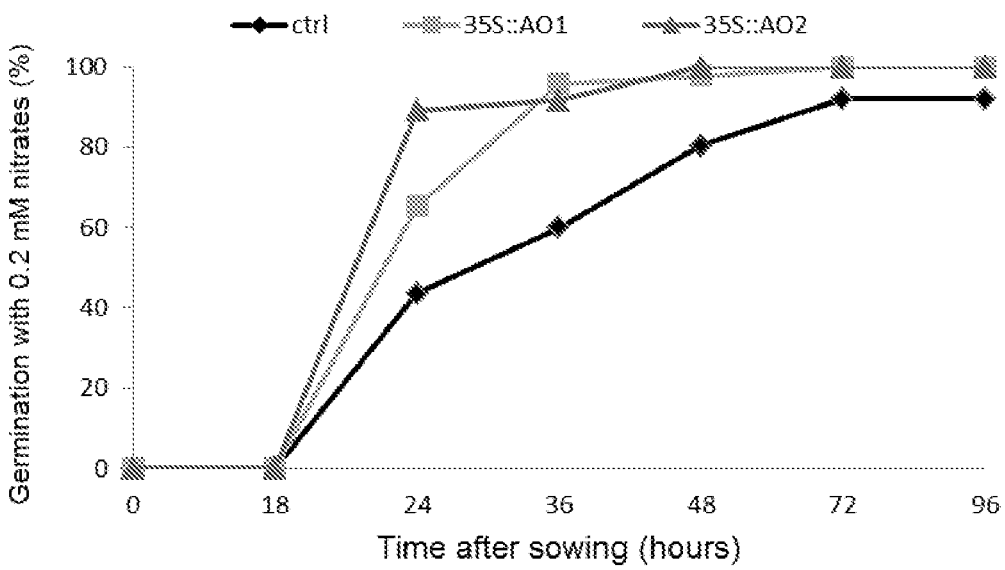

The increase in seed yield is concomitant with increased germination quality. Indeed, seeds produced by plants overexpressing L-aspartate oxidase germinate faster than control seeds (FIG. 11). The germination capacity of plants overexpressing L-aspartate oxidase is not modified in a nitrogen-poor environment as is observed for control seeds (FIG. 11). Overexpression of L-aspartate oxidase thus stimulates germination, and seeds can germinate better under nitrogen-deficient conditions.

Figure 10:
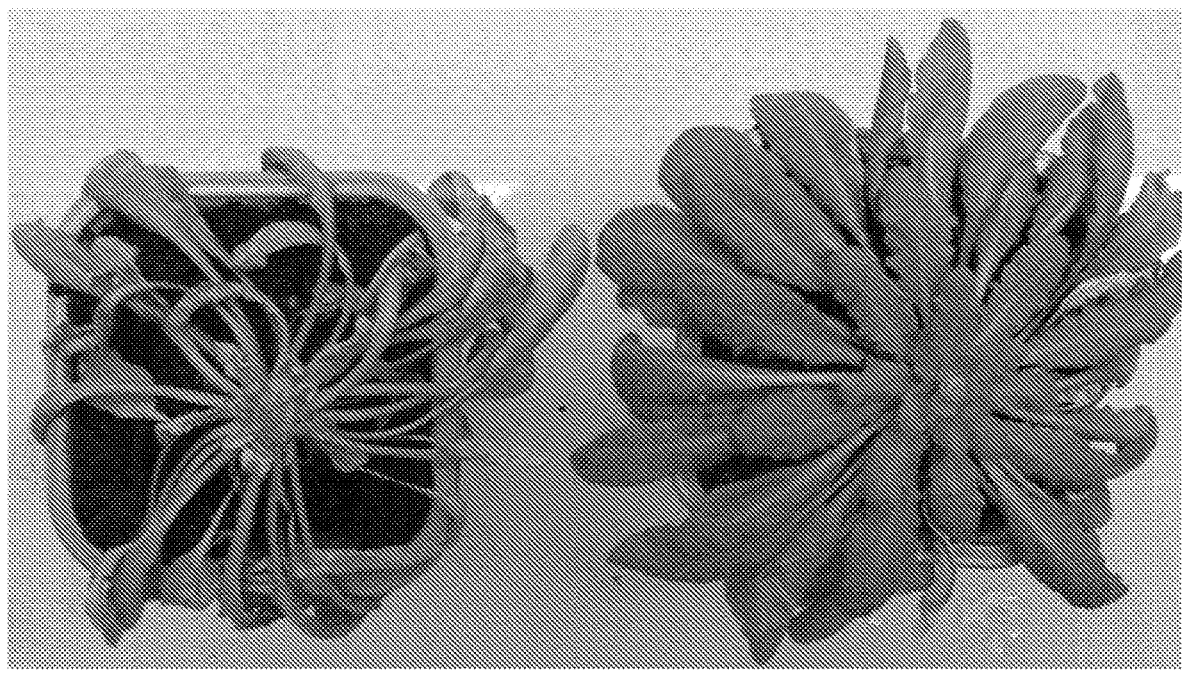
FIG. 10 is a photograph of control plants (ctrl) and of plants overexpressing L-aspartate oxidase (35S::AO) under abiotic stress conditions corresponding to intense heat combined with intense light.

Plants overexpressing L-aspartate oxidase continuously exposed to 350 µmol photons/m$^2$/s and 37° C. survived whereas control plants dried out and died under the same extreme conditions (FIG. 10). Overexpression of L-aspartate oxidase thus strengthens the resistance of plants to severe abiotic stress conditions.

Figure 12:
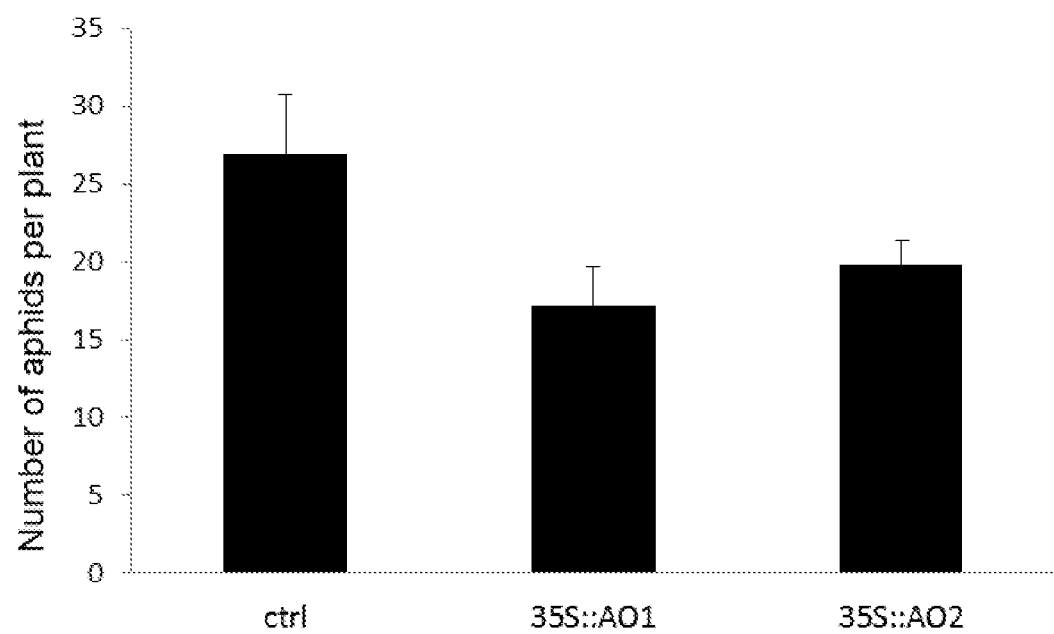
FIG. 12 is a graph representing biotic stress conditions corresponding to proliferation of *Myzus persicae* aphids on control plants (ctrl) and on plants overexpressing L-aspartate oxidase (35S::AO1 and 35S::AO2).

Plants overexpressing L-aspartate oxidase cultivated in the presence of *Myzus persicae* aphids limited aphid development in relation to control plants infested under the same conditions (FIG. 12). Overexpression of L-aspartate oxidase thus strengthens the resistance of plants to biotic stress conditions such as aphid attack.

The invention claimed is:

1. A method for improving at least one phenotypic trait of a plant, said method comprising introgression of a nucleic acid sequence into the plant, wherein the nucleic acid sequence comprises a sequence encoding L-aspartate oxidase and comprises an exogenous promoter functionally linked to the sequence encoding L-aspartate oxidase,
   wherein the at least one phenotypic trait is one or more selected from the group consisting of biomass, yield, abiotic stress resistance, biotic stress resistance, germination rate and growth rate,
   wherein the nucleic acid sequence is present in a genome,
   wherein the resulting plant overexpresses L-aspartate oxidase, and
   wherein the overexpression of L-aspartate oxidase leads to increased amounts of NAD and derivatives thereof,
   wherein the sequence encoding L-aspartate oxidase comprises SEQ ID NO: 1.

2. The method according to claim 1, further comprising cultivation of the plant to maturity, wherein the method improves the yield of the plant.

3. The method according to claim 1, further comprising cultivation of the plant to maturity, wherein the method improves the biomass production of the plant.

4. The method according to claim 1, further comprising cultivation of the plant to maturity, wherein the method improves the abiotic stress resistance and/or the biotic stress resistance of the plant.

5. The method according to claim 1, wherein the plant is selected from the group consisting of wheat, barley, rice, maize, sorghum, sunflower, rapeseed, soybean, cotton, pea, common bean, cassava, mango, banana, potato, tomato, pepper, melon, zucchini, watermelon, lettuce, cabbage, eggplant, and poplar.

6. A method for producing a plant exhibiting at least one improved phenotypic trait, comprising detection of the presence of a genetic element, linked to overexpression of L-aspartate oxidase in a donor plant, and transfer of the genetic element, linked to overexpression of L-aspartate oxidase in the donor plant thus detected, from the donor plant to a recipient plant,
   wherein the at least one phenotypic trait is one or more selected from the group consisting of biomass, yield, abiotic stress resistance, biotic stress resistance, germination rate and growth rate,
   and wherein the genetic element comprises SEQ ID NO: 1.

7. The method according to claim 6, wherein detection is carried out by measuring L-aspartate oxidase enzymatic activity in the donor plant.

8. The method according to claim 1, wherein the method comprises:

a) Providing a plant having a given level of expression of L-aspartate oxidase,
b) Providing a plant having an increased level of expression of L-aspartate oxidase in relation to the plant provided in a),
c) Crossing the plant provided in a) with the plant provided in b),
d) Generating progeny resulting from the crossing c),
e) Selecting among the progeny at least one plant having a higher level of expression of L-aspartate oxidase than that of the plant provided in b).

9. The method according to claim 8 comprising an additional step of crossing the plant selected in e) with the plant provided in b) followed by an additional step of selecting among the progeny produced at least one plant having a higher level of expression of L-aspartate oxidase than that of the plant selected in e).

10. A method for improving at least one phenotypic trait of a plant, said method comprising introgression of a nucleic acid sequence into the plant, wherein the nucleic acid sequence comprises a sequence encoding L-aspartate oxidase and comprises an exogenous promoter functionally linked to the sequence encoding L-aspartate oxidase,
    wherein the at least one phenotypic trait is one or more selected from the group consisting of biomass, yield, abiotic stress resistance, biotic stress resistance, germination rate and growth rate,
    wherein the nucleic acid sequence is present in a genome,
    wherein the resulting plant overexpresses L-aspartate oxidase, and
    wherein the overexpression of L-aspartate oxidase leads to increased amounts of NAD and derivatives thereof,
    wherein the sequence encoding L-aspartate oxidase comprises SEQ ID NO: 1.

11. The method according to claim 1, wherein the genetic element comprises a sequence having at least 90% homology with SEQ ID NO:1.

12. The method according to claim 1, wherein the genetic element comprises a sequence having at least 95% homology with SEQ ID NO:1.

13. The method according to claim 1, wherein the genetic element comprises a sequence having at least 98% homology with SEQ ID NO:1.

14. The method according to claim 6, wherein the genetic element comprises a sequence having at least 90% homology with SEQ ID NO:1.

15. The method according to claim 6, wherein the genetic element comprises a sequence having at least 95% homology with SEQ ID NO:1.

16. The method according to claim 6, wherein the genetic element comprises a sequence having at least 98% homology with SEQ ID NO:1.

* * * * *